(12) United States Patent
Hajimiri et al.

(10) Patent No.: US 8,993,236 B2
(45) Date of Patent: Mar. 31, 2015

(54) ELECTROMAGNETIC MOLECULAR SENSORS AND METHODS OF USING SAME

(75) Inventors: Seyed Ali Hajimiri, Pasadena, CA (US); Hua Wang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 338 days.

(21) Appl. No.: 12/762,229

(22) Filed: Apr. 16, 2010

(65) Prior Publication Data

US 2010/0267169 A1  Oct. 21, 2010

Related U.S. Application Data

(60) Provisional application No. 61/170,547, filed on Apr. 17, 2009.

(51) Int. Cl.
   *C12Q 1/68* (2006.01)
   *G01N 27/74* (2006.01)
   *G01N 27/72* (2006.01)
   (Continued)

(52) U.S. Cl.
   CPC ........ *G01N 27/745* (2013.01); *C12Q 2525/301* (2013.01); *C12Q 2525/197* (2013.01); *C12Q 2525/161* (2013.01); *C12Q 1/6813* (2013.01); *C12Q 1/6832* (2013.01); *C12Q 1/6834* (2013.01); *C12Q 1/6825* (2013.01); *C12Q 1/6816* (2013.01); *C12Q 2563/143* (2013.01); *C12Q 2565/519* (2013.01); *G01N 27/72* (2013.01); *G01N 33/54326* (2013.01); *G01N 33/54333* (2013.01); *G01N 2446/00* (2013.01); *G01N 27/3278* (2013.01)

USPC ........... 435/6.11; 435/6.1; 435/7.1; 436/526; 436/518; 436/524; 436/525; 436/532

(58) Field of Classification Search
   USPC .................. 436/518, 524, 525, 526, 532, 806; 435/4, 6.1–7.1
   See application file for complete search history.

(56) References Cited

U.S. PATENT DOCUMENTS 6,090,552 A * 7/2000 Nazarenko et al. .......... 435/6.12
6,303,316 B1 * 10/2001 Kiel et al. .................... 435/6.19

(Continued)

FOREIGN PATENT DOCUMENTS

EP    2017619          1/2009
EP    2060637 A1 *    5/2009

(Continued)

OTHER PUBLICATIONS

International Search Report and Written Opinion for PCT Application No. PCT/US2010/031517 dated Nov. 9, 2010.

*Primary Examiner* — Melanie Y Brown
*Assistant Examiner* — Erik B Crawford
(74) *Attorney, Agent, or Firm* — Knobbe, Martens, Olson & Bear LLP

(57) ABSTRACT

Devices having an electromagnetic detector for the detection of analytes are disclosed. The devices include an electromagnetic detector, including effective inductance-change magnetic detectors, and a binding moiety. The device can include an electromagnetic material that can be detected by the detector. The device is configured such that binding of an analyte to the binding moiety changes the relationship between the electromagnetic detector and the electromagnetic material such that a change in electromagnetic field is detected by the electromagnetic detector.

19 Claims, 16 Drawing Sheets

(51) Int. Cl.
*G01N 33/543* (2006.01)
*G01N 27/327* (2006.01)

(56) References Cited

U.S. PATENT DOCUMENTS

| | | | |
|---|---|---|---|
| 2003/0059955 | A1 | 3/2003 | Bamdad |
| 2005/0087000 | A1 | 4/2005 | Coehoorn et al. |
| 2006/0003371 | A1* | 1/2006 | Russell et al. ............ 435/6 |
| 2006/0240416 | A1* | 10/2006 | Banerjee et al. ............ 435/6 |
| 2007/0172890 | A1* | 7/2007 | Prins et al. ............ 435/7.1 |
| 2008/0206104 | A1 | 8/2008 | Prins et al. |
| 2008/0207464 | A1 | 8/2008 | Prins et al. |

FOREIGN PATENT DOCUMENTS

| | | |
|---|---|---|
| WO | WO 2006131892 A2 * | 12/2006 |
| WO | WO 2007092909 A2 * | 8/2007 |

\* cited by examiner

ELECTROMAGNETIC MOLECULAR SENSORS AND METHODS OF USING SAME

CROSS-REFERENCE TO RELATED APPLICATIONS

This application claims priority from U.S. Provisional No. 61/170,547, filed Apr. 17, 2009, the contents of which application is incorporated herein by reference in its entirety.

BACKGROUND OF THE INVENTION

1. Field of the Invention

The invention relates to the field of detection of analytes using electromagnetic detection.

2. Description of the Related Art

Recently, novel molecular-level detection schemes have attracted great interest in many fields, such as biology, chemistry and applied physics. However, most currently developed detection methods rely on first attaching certain sensing tags onto the target molecules and then detecting the presence of these tags to indirectly infer the information about the target molecules. A common example of such is a fluorescent tags attached to the target molecules. However, label-tagging processes required by currently developed detection methods thus introduce several impediments described as follows.

First of all, the label-tagging processes normally require several chemical steps which complicate the design and operation of the sensor system and fundamentally limit the sensor integration level. Also those chemical steps could be time-consuming and lead to prolonged sensing time. This significantly limits the total throughputs of the sensor system per given time.

Secondly, these label-tagging processes can degrade the sensor accuracy, since only a limited tagging efficiency (instead of 100%) can be achieved practically. This means that some of the target molecules will not be tagged with the labels and therefore cannot be sensed by the sensors, resulting in "false negative" detection errors. Also free labels with no target molecules may also remain in the samples after the tagging process, which will be detected by the sensor and lead to "false positive" detection errors.

Moreover, the attached labels will inevitably alter the chemical and/or physical properties of the target molecules. For example, the chemical dynamics and the physical diffusion properties of the target molecules can be dramatically changed when attached to certain molecular tags. These include the cases when the tags are of large molecular mass and/or excessive electrical charge and/or certain hydrophilic/hydrophobic properties. This interference effect due to the labels therefore inhibits further studies of the target molecules.

Furthermore, those molecular labels and their corresponding buffers could be costly when used in large quantities. And for each complete operation of the sensor, those molecular labels and their corresponding buffers are used as consumables and needed to be replenished. This is exacerbated in high throughput parallel sensing, commonly performed in today's bioassays. Therefore, the system cost may be significantly increased due to the labels and buffers.

Improved techniques for detection of molecules are clearly needed, including techniques that do not require labeling of the target molecules.

SUMMARY OF THE INVENTION

In some embodiments, a detection device comprising: an electromagnetic detector; a first binding moiety; and an electromagnetic material is provided, wherein the device is configured such that binding of an analyte to the binding moiety changes the relationship between the electromagnetic detector and the electromagnetic material such that a change in electromagnetic field is detected by the electromagnetic detector. In some embodiments, the electromagnetic detector is covalently linked to the binding moiety. In some embodiments, the binding moiety is covalently linked to the electromagnetic material. In some embodiments, both the binding moiety and the electromagnetic material are covalently linked to the electromagnetic detector. In some embodiments, the binding moiety is covalently linked to the electromagnetic material.

In some embodiments, a detection device further comprises a magnet, electromagnet, or electrode, wherein the electromagnetic material is situated between the electromagnetic detector and the magnet, electromagnet or electrode.

In some embodiments, the electromagnetic material is buoyant.

In some embodiments, the electromagnetic material is a charged particle, a magnetic particle, or a particle with a dipole. In some embodiments, the electromagnetic material is a ferromagnetic bead or a superparamagnetic bead. In some embodiments, the electromagnetic material is a chelator. In some embodiments, the electromagnetic material is ferritin.

In some embodiments, the detector produces an electric signal.

In some embodiments, the device further comprises a second binding moiety. In some embodiments in which the device has a second binding moiety, the first binding moiety is linked to the electromagnetic detector, the second binding moiety is linked to the electromagnetic moiety; and the first and second binding moieties bind to the same analyte at the same time. In some embodiments in which the device has a second binding moiety, the first binding moiety and second binding moieties are covalently linked.

In some embodiments in which the device has a second binding moiety, wherein the first binding moiety and second binding moiety are nucleic acids.

In some embodiments, the electromagnetic detector is a magnetic detector. In some embodiments, the electromagnetic detector is a GMR, Hall effect, or effective-inductance change magnetic detector.

In some embodiments, the binding moiety is a protein. In some embodiments, the binding moiety is an antibody. In some embodiments, the binding moiety is a nucleic acid.

In some embodiments, the analyte is a nucleic acid. In some embodiments, the binding moiety is a nucleic acid and the analyte is a nucleic acid.

In some embodiments, the binding moiety is a nucleic acid that internally hybridizes in the absence of the analyte. In some embodiments, the binding moiety is a nucleic acid, the binding moiety is an aptamer.

In some embodiments, the first binding moiety and the second binding moiety bind the same analyte. In some embodiments, the first binding moiety and the second binding moiety are the same. In some embodiments, the first binding moiety and the second binding moiety are different. In some embodiments, the first and the second binding moiety are covalently linked.

In some embodiments, the device includes one or more linkers. In some embodiments, the linker is attached to the binding moiety. In some embodiments, a linker is attached to the first and second binding moieties. In some embodiments a linker is attached to a binding moiety and the electromagnetic material. In some embodiments, a linker is attached to the detector and a binding moiety. In some embodiments, a linker is attached to one or more binding moieties.

In some embodiments, method of detecting an analyte is provided, the method comprises: contacting a sample that may contain an analyte with a detection device, wherein the detection device comprises: an electromagnetic detector, a first binding moiety; and an electromagnetic material, wherein the device is configured such that binding of an analyte to the binding moiety changes the relationship between the electromagnetic detector and the electromagnetic material such that a change in electromagnetic field is detected by the electromagnetic detector; and measuring a signal from the electromagnetic detection device.

In some embodiments, the electromagnetic detector is a GMR, Hall effect, or effective-inductance change magnetic detector. In some embodiments, the electromagnetic detector is covalently linked to the binding moiety. In some embodiments, the binding moiety is covalently linked to the electromagnetic material. In some embodiments, the device further comprises a magnet, electromagnet, or electrode, and wherein the electromagnetic material is situated between the electromagnetic detector and the magnet, electromagnet or electrode. In some embodiments, the method further comprises applying a force to the electromagnetic material using the magnet, electromagnet or electrode.

In some embodiments, the binding moiety is a protein. In some embodiments, the binding moiety is an antibody. In some embodiments, the binding moiety is a nucleic acid. In some embodiments, the binding moiety is an aptamer.

In some embodiments, the analyte is a nucleic acid. In some embodiments, the binding moiety is a nucleic acid and the analyte is a nucleic acid.

In some embodiments, the binding moiety is a nucleic acid that internally hybridizes in the absence of the analyte.

In some embodiments, the device further comprises a second binding moiety. In some embodiments, the first binding moiety and the second binding moiety bind the same analyte. In some embodiments, the first binding moiety and the second binding moiety are the same. In some embodiments, the first binding moiety and the second binding moiety are different. In some embodiments, the first and the second binding moiety are covalently linked.

DETAILED DESCRIPTION OF THE PREFERRED EMBODIMENT

Figure 1:
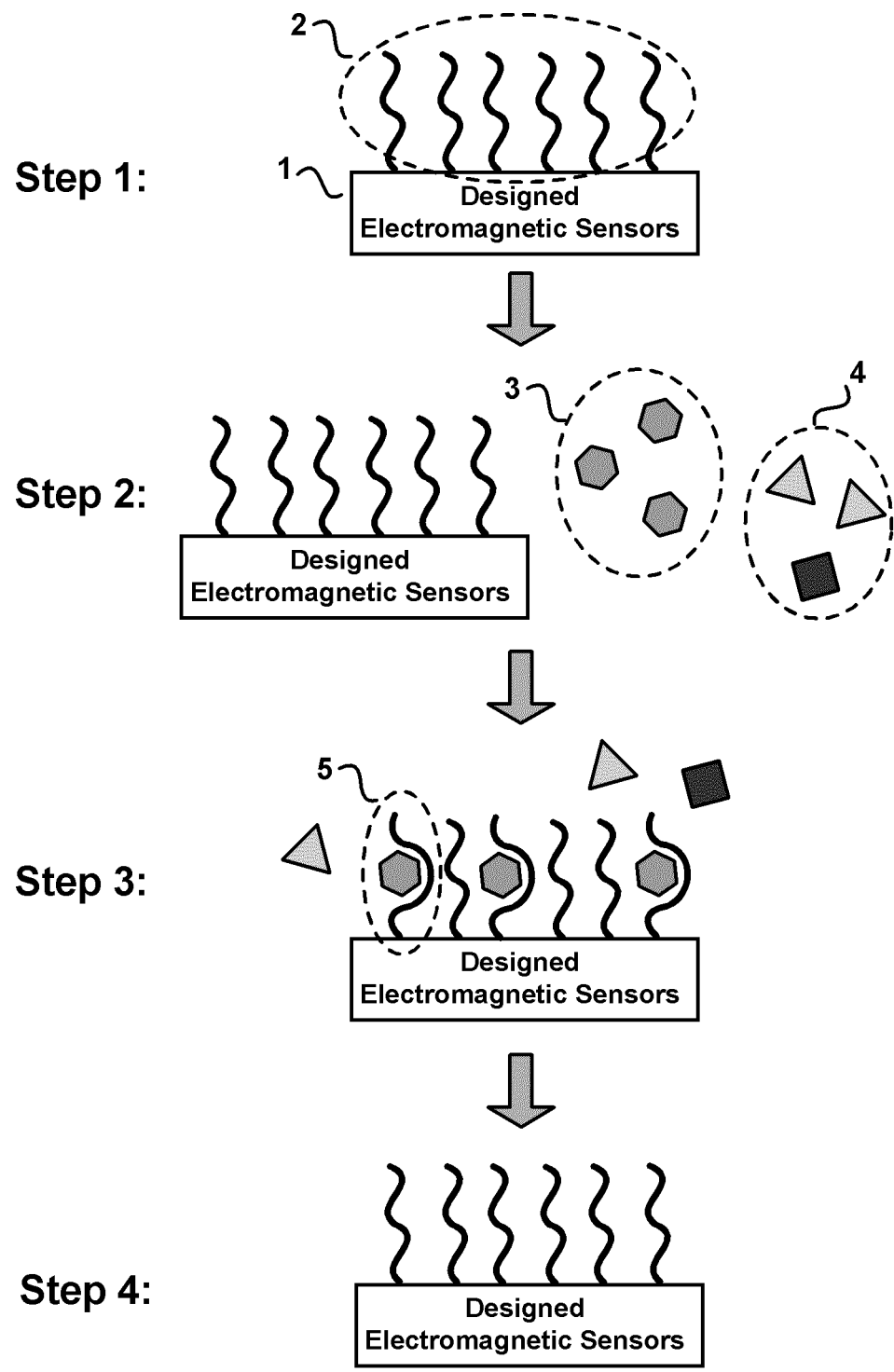
FIG. 1 illustrates a general electromagnetic label-free molecular detection method.

In some embodiments, a detection device has an electromagnetic detector and a binding moiety, configured such that binding of an analyte to the binding moiety produces a detectable change in the electromagnetic field that is sensed by the electromagnetic detector. The binding moiety is typically attached to a surface of the electromagnetic detector, either covalently or non-covalently (e.g., through adsorption). In some embodiments, the detection device also includes an electromagnetic material. In some embodiments, the electromagnetic material is attached to the binding moiety. In some such embodiments, binding of an analyte to the binding moiety can produce a change in the relationship between the electromagnetic material and the electromagnetic detector, such that a signal can be detected on binding of the analyte.

Definitions

The term "antibody protein" is used herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Types of antibodies, including antibody isotypes, monoclonal antibodies and antigen-binding fragments thereof (e.g., Fab, Fv, scFv, and Fd fragments, chimeric antibodies, humanized antibodies, single-chain antibodies, etc) are known and need not be described in any further detail.

An "aptamer" may be a nucleic acid molecule, such as RNA or DNA that is capable of binding to a specific molecule with high affinity and specificity (Ellington et al., Nature 346, 818-22 (1990); and Tuerk et al., Science 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes.

The term "binding moiety" refers to an agent that binds a target molecule or analyte through an interaction that is sufficient to permit the agent to bind and concentrate the target molecule from a homogeneous mixture of different molecules. The binding interaction is typically mediated by an affinity region of the binding moiety. Typical binding moieties include any moiety that can specifically bind to a target molecule. In certain embodiments, a polypeptide, e.g., an antibody protein, may be employed. Binding moieties usually "specifically bind" a target molecule. Accordingly, the term "binding moiety" refers to a molecule or a multi-molecular complex which can specifically bind a target molecule, e.g., a phosphorylated polypeptide, with a dissociation constant (KD) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to up to about $10^{-16}$ M) without significantly binding to other molecules. The term "specific binding" refers to the ability of a capture agent to preferentially bind to a particular target molecule that is present in a homogeneous mixture of different target molecule. In certain embodiments, a specific binding interaction will discriminate between desirable and undesirable target molecules in a sample, typically more than about 10 to 100-fold or more (e.g., more than about 1000- or 10,000-fold).

"Complementary" means with respect to a nucleic acid the ability to hybridize to another nucleic acid, including, for example, a target molecule. A nucleic acid generally is complementary based on the interaction of corresponding Watson-Crick base pairs, for example, A-T, A-U, C-G, G-C, U-A and T-A, but also can include interactions between any other nucleotides. Complementary includes a nucleic acid that is entirely Watson-Crick base paired to another nucleic acid, or has one or more mismatched base pairs. In some embodiments, complementary includes nucleic acids that bind under stringent conditions to a target molecule.

"Do/does not bind" as used herein to describe binding moiety-analyte binding, does not mean that there is absolutely no binding at all. Compared to an binding moiety that does bind the analyte, the Ka (association constant for binding between binding moiety and the analyte) for the binding moiety that "does not bind" the aptamer is at least about 10-fold, 100-fold, 1000-fold or more larger than that of the a binding moiety that binds to the analyte, and thus its binding affinity for the analyte is at least about 10-fold, 100-fold, 1000-fold or more weaker than that of the binding moiety that binds to the analyte.

"GMR" or "giant magnetoresistance" means quantum mechanical magnetoresistance effect observed in thin film structures composed of alternating ferromagnetic and non-magnetic layers, which often changes the effective electrical resistance of the thin film in the presence of an external magnetic field.

"Hall effect" means the production of a voltage difference (the Hall voltage) across an electrical conductor, transverse to an electric current in the conductor and a magnetic field perpendicular to the current.

The terms "hybridize" and "hybridization" refer to the formation of complexes between nucleotide sequences which are sufficiently complementary to form complexes via Watson-Crick base pairing.

"Nucleic acid," "nucleic acid sequence," "nucleic acid molecule," and "polynucleotide" refer to a DNA sequence or analog thereof, or an RNA sequence or analog thereof, or combinations thereof, including chimeric molecules. Nucleic acids are formed from nucleotides, including, but not limited to, the nucleotides listed below. A polynucleotide may include analogs of DNA or RNA having modifications to either the bases or the backbone. For example, polynucleotides, as used herein, includes the use of peptide nucleic acids (PNA), phosphorothioates, phosphoramides, phosphorodithioates, O-methylphosphoroamidites, and any other modifications to the backbone.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N-6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

The term "stringent conditions" refers to conditions under which a nucleic acid will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an detector surface between complementary binding members, e.g., between a nucleic acid binding moiety and complementary targets in a sample, e.g., nucleic acid probes, such as DNA probes, and their corresponding nucleic acid targets that are present in the sample, e.g., their corresponding mRNA or DNA analytes present in the sample.

Detection Devices

In some embodiments, a detection device has an electromagnetic detector and a binding moiety, configured such that binding of an analyte to the binding moiety produces a detectable change in the electromagnetic field that is sensed by the electromagnetic detector. The binding moiety is typically attached to a surface of the electromagnetic detector, either covalently or non-covalently (e.g., through adsorption). In some embodiments, the detection device also includes an electromagnetic material. In some embodiments, the electromagnetic material is attached to the binding moiety. In some such embodiments, binding of an analyte to the binding moiety can produce a change in the relationship between the electromagnetic material and the electromagnetic detector, such that a signal can be detected on binding of the analyte.

In one embodiment, the binding moiety is prepared on a substrate surface, and an electromagnetic detector is placed adjacent to the substrate. In some embodiments, the electromagnetic detector is bonded to such a substrate.

Referring to FIG. 1, in step 1, the electromagnetic sensor 1, is pre-deposited with binding moieties 2. The probe molecules can either be detectable by the electromagnetic detector because of their inherent electrical and/or magnetic properties, or can be modified to exhibit certain electrical and/or magnetic properties. In step 2, the sensing samples are introduced to the sensor system. The sensing samples may include target molecules 3 and/or interference molecules 4. Interference molecules are molecules that do not bind to the binding moiety 2. In step 3, the probe molecules then interact with the present target molecules in the sample to form complex 5 and lead to certain conformational/structural changes. These changes then lead to the effective electrical and/or magnetic properties changes of the sensing environment presented to the sensor resulting in certain sensor output signal change. Thus, the presence of the target molecules, both qualitatively and quantitatively, can be determined from changes in the sensor output signal.

Figure 2:
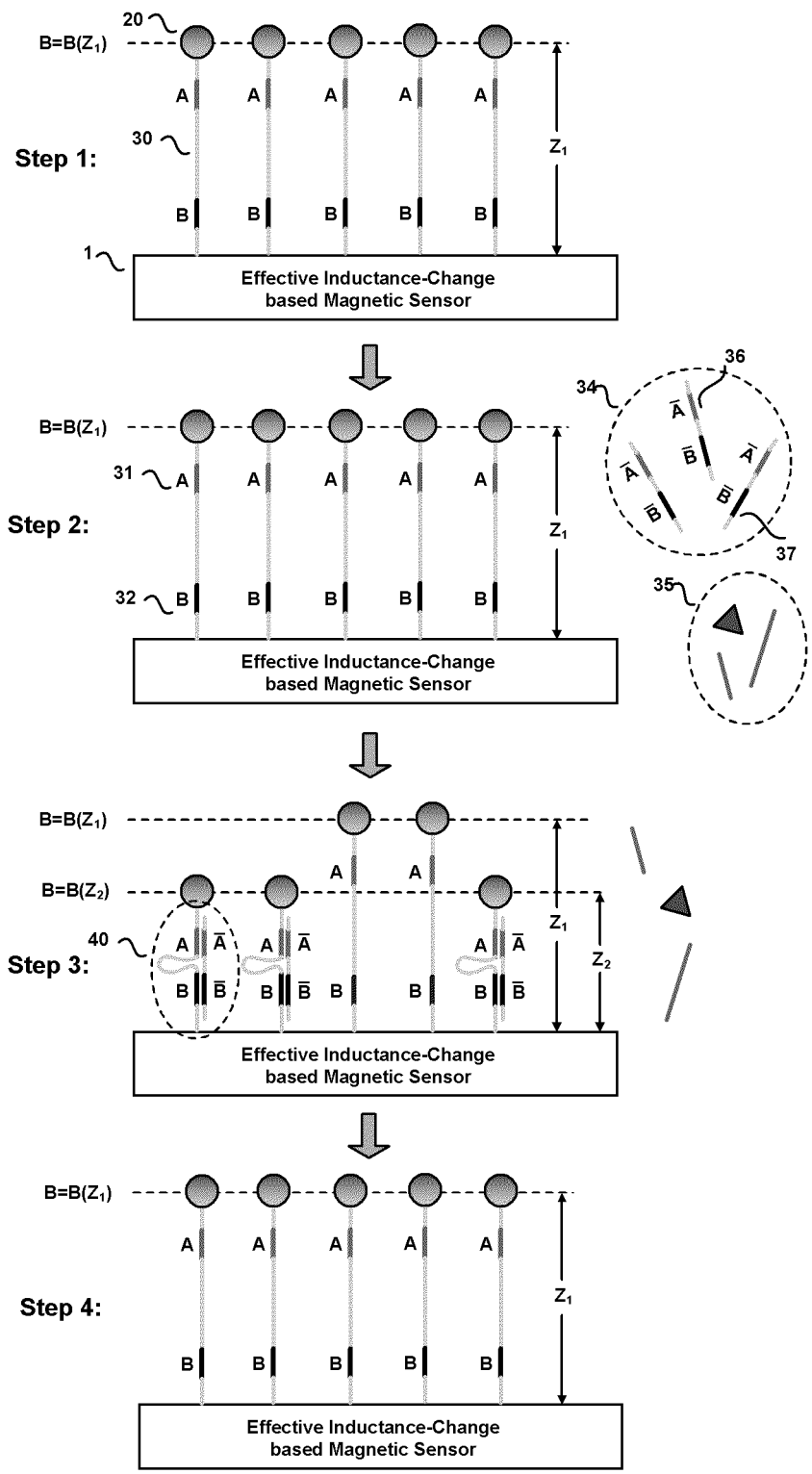
FIG. 2 illustrates a label-free detection method and device, having an electromagnetic material and detector, with two binding moieties.
Figure 3:
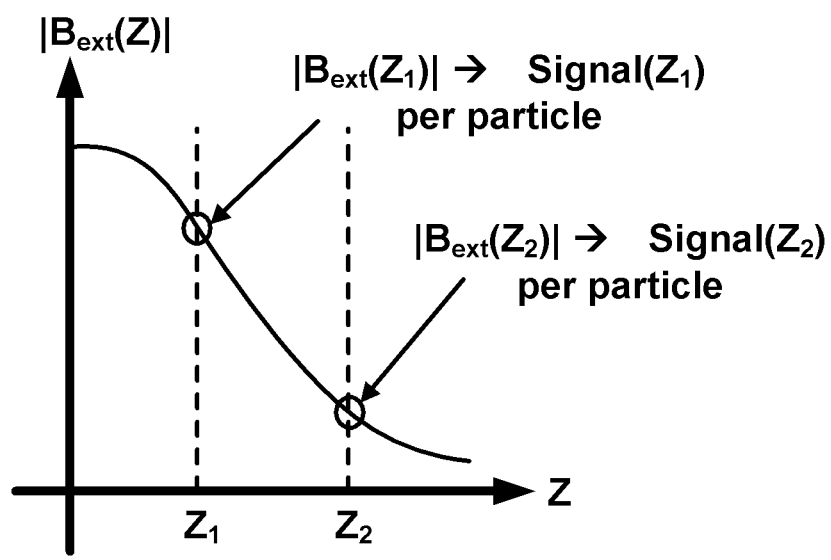
FIG. 3 shows the spatial dependent sensor signal (per particle) due to the spatial dependent excitation magnetic field generated by the sensor.

Referring to FIG. 2, a detector system is shown that includes electromagnetic detector 1 that is an effective-inductance-change based magnetic sensor. A single-stranded nucleic acid probe nucleic acid 30 is attached to the detector, and has two binding moieties 31 and 32 that are complementary to target nucleic acids 34. Samples can be introduced that contain target nucleic acids and interfering molecules 35. On binding of the target molecules to the probe, a complex 40 is formed. In this embodiment, binding moieties 31 (A) and 32 (B) form doubles stranded regions with the complementary regions of the target molecule 34 and complementary regions 36 and 37, and leave a loop of the intervening linker separating the binding moieties. Thus, binding of the target molecule to the probe results in a conformation change that brings electromagnetic material 20 closer to the surface of the electromagnetic detector. In such an embodiment, the sensing mechanism relies on the fact that the excitation magnetic field from the effective-inductance-change magnetic sensor varies for positions with different distances from the sensor surface. This spatial magnetic field variation leads to different sensor signal levels if the magnetic particles are located at those positions with different excitation magnetic field strength. This is conceptually illustrated in FIG. 3. While the binding moieties 31 and 32 are shown with a linker region separating them, no linker is necessary, as binding of a complementary target molecule will result in a conformational change (single strand to double strand) that changes the relative position of the electromagnetic material to the electromagnetic detector.

In the embodiment shown in FIG. 2, the sensing procedures are described as follows. In Step 1, the sensor together with the probe molecules are prepared. At this step, since all the probe DNAs are in their free-state conformation, the magnetic particles are largely distributed with a distance $Z_1$ from the sensor surface, and present a sensor signal Signal($Z_1$) determined by the excitation magnetic field of B($Z_1$). Then in Step 2, the test samples are introduced to the sensor which potentially including the target molecules (block 5) and interference molecules (bock 4) are then introduced. Due to the fact that the target molecules have piece-wise complementary DNA sequence with the probe DNAs, the interactions between them form new complexes, denoted as block 3 in the Step 3. This formation essentially changes the conformation/structure of the probe molecules and therefore leads to the corresponding magnetic particles distributed in a different distance, as $Z_2$, from the sensor surface. This leads to the total sensor signal change from Signal($Z_1$) to Signal($Z_2$). And this signal change is proportional to the overall numbers/concentration of the target molecules presented in the sample. Step 4, as an optional step, shows that after proper washing, both the target molecules and the interference molecules can be removed from the sensor surface and the sensor surface can be recovered to allow reuse of the sensor.

Applying Forces to the Sensor

In some embodiments, a starting configuration of the detection system is achieved through application of a force on the electromagnetic material and/or binding moieties. Such a force can be applied passively or actively. In some embodiments, the force is applied to maintain the binding moieties (e.g., probe nucleic acid) in an extended conformation in the absence of binding to a target molecule. Forces can be applied using electrodes, electromagnets, or permanent magnets. In some embodiments forces can be applied by the composition or configuration of the device. For example, in some embodiments, the binding moiety can have a particle attached to it with density greater than or less than the solution in which the assay is performed. Buoyancy of such a particle and gravity can apply forces to the electromagnetic material.

In one embodiment, a force 7 is applied to the electromagnetic material 20. In one embodiment, the force is applied with an external electromagnet or permanent magnet exerting force on the strands. The force applied can be varied in the case of an electromagnet or electric field by control of the current or voltage passed through the magnet or electrode. In the case of a permanent magnet, the force applied can be altered by changing the physical relationship of the magnet and the electromagnetic material. In one embodiment, the permanent magnet is slidably mounted on the detection device. The force applied can be controlled by a microprocessor or computer. For example, a controller can move a physical magnet or change the voltage or current applied to an electromagnet, to vary the magnetic field applied to electromagnetic material.

In some embodiments, a force is applied to the system by placing the sensor in an orientation in which a particle attached to the binding moiety is below the sensor surface. In such embodiments, gravity will exert a force on the elecromagnetic material away from the surface. In some embodiments, a force is applied using buoyancy of a particle attached to the binding moiety, including, for example, an electromagnetic material. In some embodiments, a force is applied using an external electric field applied that can interact with electrically charged particle. In the case of the applied electric field, the system may include an electrode or series of electrodes that are disposed on the electromagnetic detector and/or on the side of the electromagnetic materials and away from the electromagnetic detector.

Both the magnetic manipulation (such as the one provided by electromagnets) and the electrical manipulation can be controlled electrically which provide programmability of the manipulation, for example with certain pulse configurations. This can be used to facilitate the hybridization by creating an energetically more favorable condition by removing the extension forces and reapplying it only in the measurement phase.

Moreover, the gravity force can also be used to keep the probe molecules straight, if the magnetic particles process a higher density than the solution. For example, the sensor system can be flipped up-side-down (with the sensor surface facing down towards the earth) to ensure that the probe molecules labeled with magnetic particles are kept straight (as shown in the FIG. 1).

In both cases described above, when the interactions between the target molecules and the probe systems are required, for example in step 3 in FIG. 1, the aforementioned magnetic/electrical/gravitational manipulation forces can be turned-off or programmed in a certain way to bring the binding sites on the probe DNA molecules closer to each other and facilitate the interactions between the probe molecules and the target molecules. For example, the electro/permanent magnets or the electrical fields can be turned-off or removed, or the sensor system can be flipped with the sensor bottom facing down towards the earth. After certain reaction time, the manipulation forces can be applied again. For example, the electro/permanent magnets or the electrical fields can be turned-off or mounted back again, or the sensor system can be flipped back to the up-side-down position. This ensures that the probe molecules without target molecules are configured back to the extended state, such as being extended. Additionally, the buoyant forces can also be utilized to keep the probe molecules straight by attaching the magnetic particles with low density materials.

Figure 4:
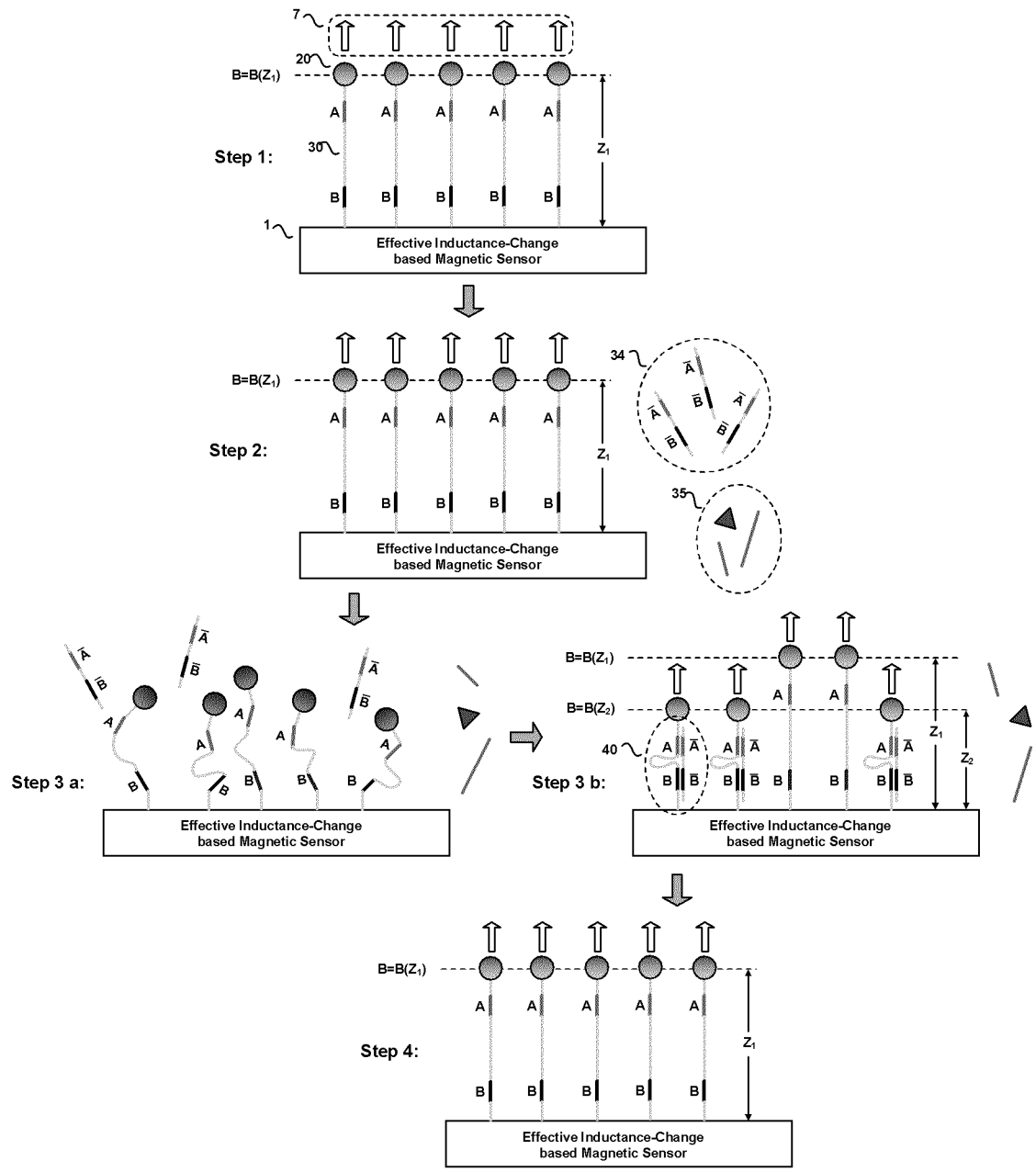
FIG. 4 shows a label-free detection method and device, having a magnetic particle and effective inductance-change detector, with two binding moieties.

The manipulation procedures together with the sensing procedures are summarized in FIG. 4. In FIG. 4, an electromagnetic detector 1 is attached to a DNA probe having two binding moieties (A and B). Manipulation forces 7, i.e. electrical/magnetic/gravitational forces described above can be applied. In one embodiment, the manipulation force is applied in Step 1, which extends the probe molecules to the desired conformation. The sensor output is measured as the baseline signal, Signal($Z_1$). Then the samples are added to the sensor system. In Step 3a, the manipulation force is turned off which facilitates the interaction between the probe molecules and the incoming target molecules. After certain reaction time, the extension force is turned back on in Step 3b which restore the unbounded probe molecules back to their initial conformation. And the sensor read-out is performed to yield the sensed signal, Signal($Z_2$). The difference between Signal($Z_1$) and Signal($Z_2$) reveals the information for the number of probe-target molecular complex formation, which is then proportional to the concentration of the target molecules in the incoming samples.

Figure 5:
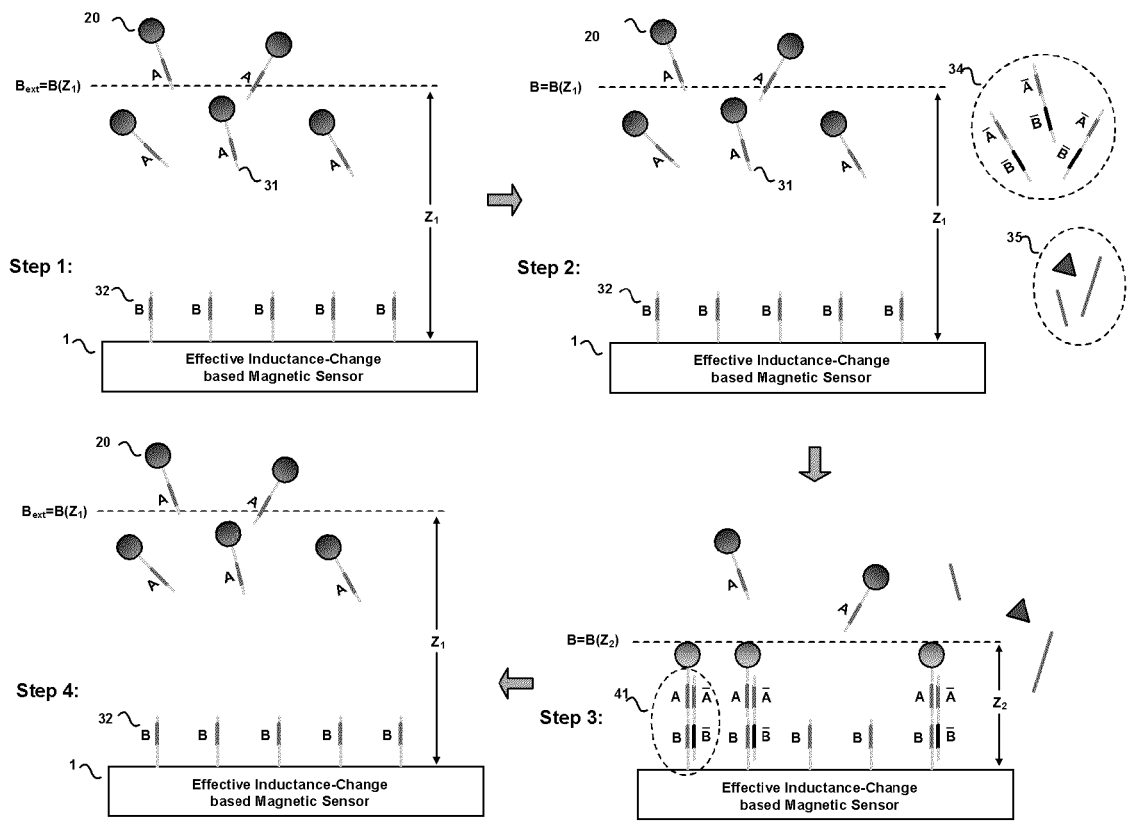
FIG. 5 illustrates a label-free detection method and device, having an electromagnetic material and an electromagnetic detector, each attached to a binding moiety that binds to a single analyte.

FIG. 5 illustrates another embodiment. An effective-inductance change magnetic sensor 1 is used. Immobilized probe molecules having a binding site 32 are single-stranded nucleic acids. Binding site 32 is complementary to a region of a target molecule 34, and can form complex 41. The system shown in FIG. 5 also includes a magnetic particle 20 having a second nucleic acid probe attached thereto, with a binding moiety 31 that is complementary to target molecule 34 at a different region than binding moiety 32. A single stranded nucleic acid target molecule 34 can bind to both the binding moiety 32 and the magnetic particle bound binding moiety 31 simultaneously. The system illustrated in FIG. 5 can detect the presence of target molecules 34 in the presence of interfering molecules 35.

In the embodiment shown in FIG. 5, the sensing procedure is described as follows. In Step 1, the sensor together with the probe molecules and the magnetically tagged elements are prepared. At this step, since all the magnetic particles are in free diffusion state, overall they have an average distance Z1 from the sensor surface, and present a sensor signal determined by the excitation magnetic field of B(Z1). Then in Step 2, the test samples are introduced to the sensor which potentially includes the target molecules 34 and interference molecules 35 are then introduced. Due to the fact that the target molecules have complementary DNA sequence with the probe DNAs and the labeled magnetic particles, the interaction between them forms new energetically favorable molecular complexes 41, formed from the target molecule and detector and bead bound probes. This formation essentially changes the conformation/structure of the probe system, in that a number of magnetic particles will be attracted onto the sensor surface and overall the magnetic particles present a different average distance of Z2, from the sensor surface compared with the baseline distance of Z1. This leads to a change in the aggregated sensor signal change, which is proportional to the overall numbers of the magnetic particle attracted onto the sensor surface and therefore proportional to the concentration of the target molecules in the sample. Therefore, by registering the signal change of the sensor, the presence of the target molecules can then be inferred both qualitatively and quantitatively. The complex 41 can optionally be disrupted by washing the sensor with high salt solution, raising the temperature or making other changes. Where the magnetic bead is not covalently attached it can be reintroduced after washing the target molecule off the sensor. In some embodiments, the magnetic particles labeled with the probe molecules may have its density higher than the solution. In some embodiments, manipulation forces are used to keep the free magnetically labeled probe molecules free for diffusion in the solution.

Figure 6:
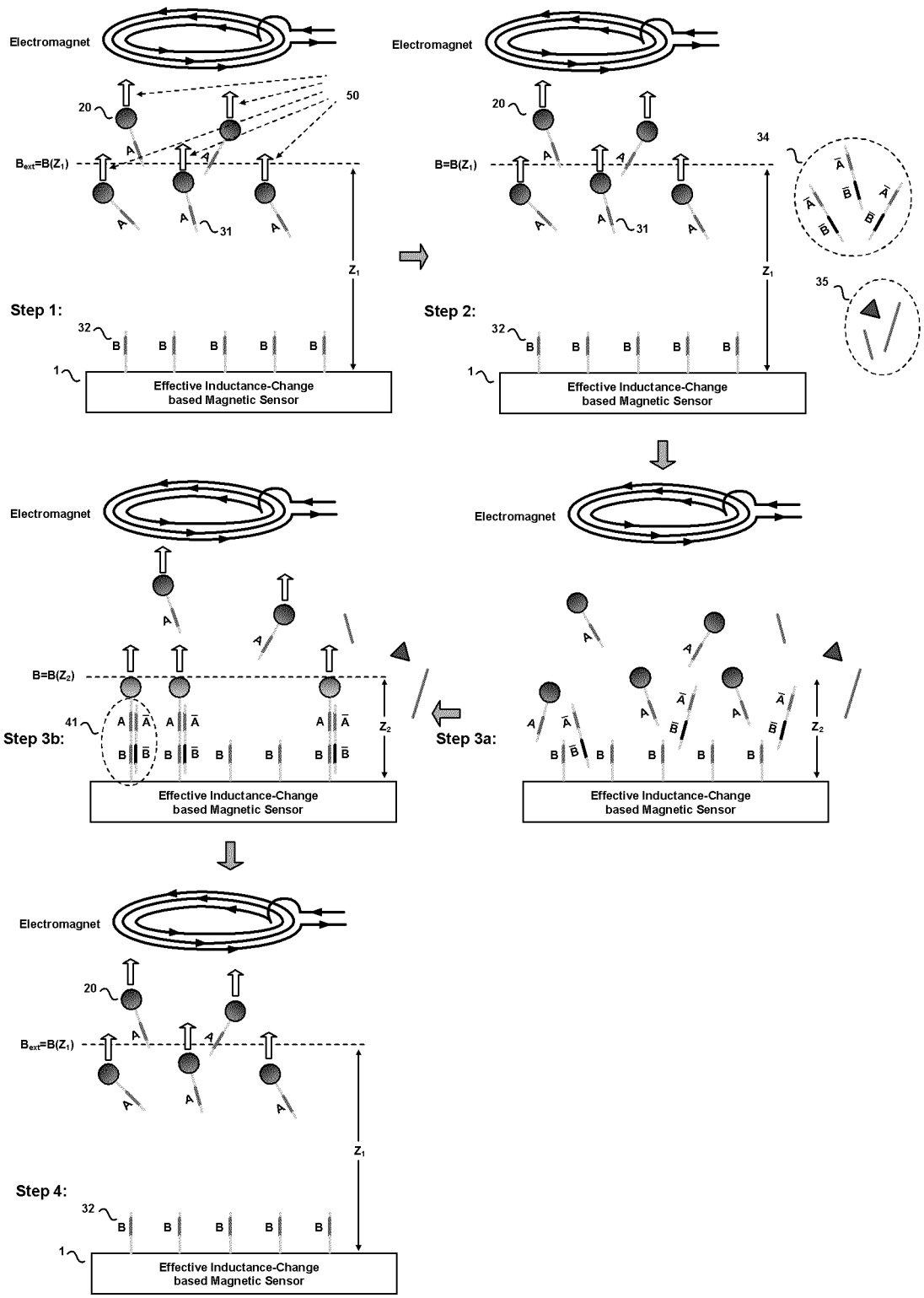
FIG. 6 illustrates a label-free detection method and device together with the probe-molecule manipulation procedures.
Figure 7:
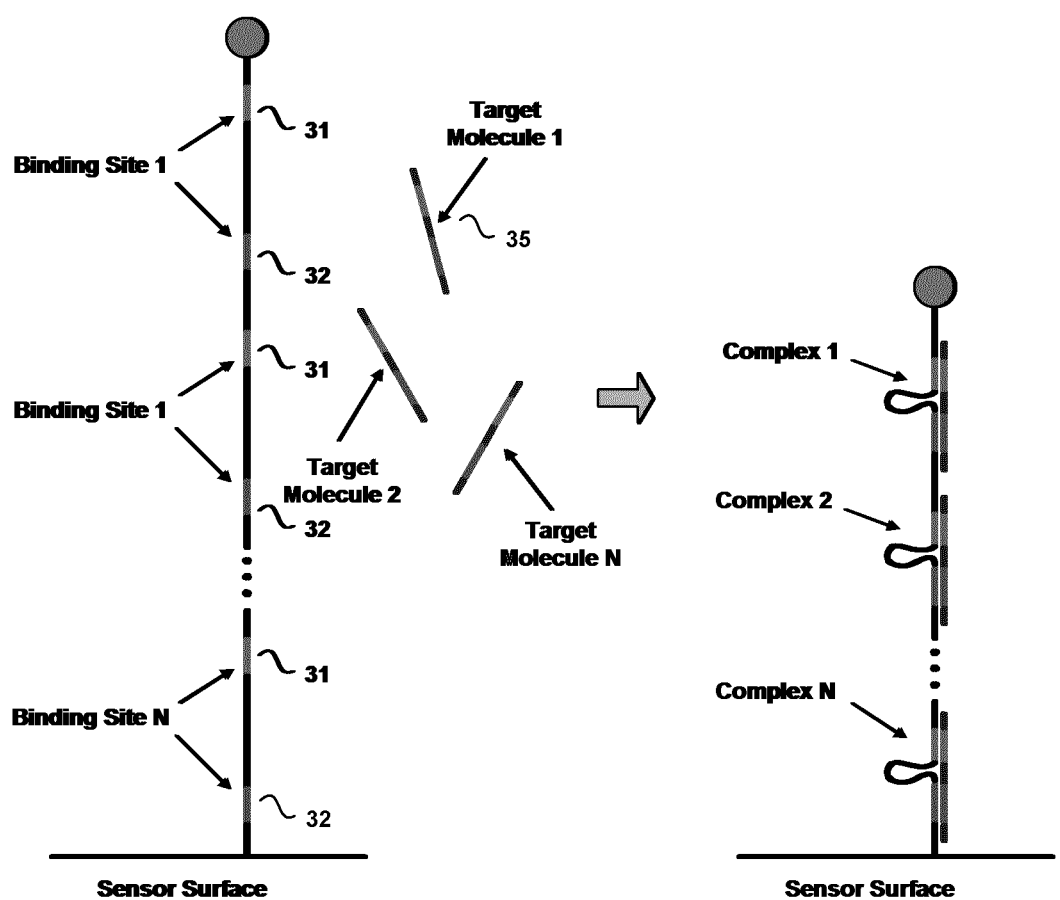
FIG. 7 illustrates a detection device having an electromagnetic detector, an electromagnetic material and a plurality of binding moieties for detecting a target molecule.

In the embodiment shown in FIG. 6, an electromagnetic detector 1, in this embodiment, an effective inductance-change magnetic sensor, is coupled to an immobilized nucleic acid probe having a binding site 32. Binding site 32 is complementary to a region of a target molecule 34. The system shown in FIG. 6 also includes a magnetic particle 20 having a second nucleic acid probe attached thereto, with a binding moiety 31 that is complementary to target molecule 34 at a different region than binding moiety 32. A single stranded nucleic acid target molecule 34 can bind to both the binding moiety 32 and the magnetic particle bound binding moiety 31 simultaneously. The system illustrated in FIG. 6 can detect the presence of target molecules 34 in the presence of interfering molecules 35. In addition, manipulation forces 7, i.e. magnetic forces from the electromagnet can be applied to the system. In the embodiment shown in FIG. 6, in Step 1, the manipulation force is on, which prevents the free magnetically labeled probes from sinking to the sensor surface. The sensor output here is measured as the baseline signal, Signal (Z1). Then the samples are added to the sensor system in Step 2. In Step 3a, the manipulation force is off which facilitates the interaction between the probe molecules (the immobilized probes and the free probes) and the incoming target molecules. After certain reaction time, the manipulation forces are turned back on in Step 3b which restore the unbounded free magnetically labeled probe molecules back to floating state and away from the sensor surface. And the sensor read-out is performed to yield the sensed signal, Signal (Z2). The difference between Signal(Z1) and Signal(Z2) thus reveals the information for the number of probe-target molecular complex formation, which is then proportional to the concentration of the target molecules in the incoming samples.

In some embodiments, the binding moiety is attached to a surface or support that can be placed near to or adjacent to an electromagnetic detector. The surface or support will have a thickness that allows the detector to detect binding events, but can prevent a solution surrounding the binding moiety from touching the. In one embodiment, a vessel 120 has a lower surface 130 to which linker 60 is attached. Linker 60 has two binding moieties 51 and 52 that are both antibodies. Linker 60 is also attached to magnetic particle 20. Vessel 120 can be placed on electromagnetic detector 1, such that magnetic particle 20 can be detected.

Electromagnetic Detectors

Magnetic Detectors

In some embodiments, the magnetic detector is selected from a GMR, Hall Effect, or effective inductance detector.

GMR sensors are known to one of skill in the art. The GMR sensor utilizes a quantum mechanical magnetoresistance effect often observed in thin film structures composed of alternating ferromagnetic and nonmagnetic layers, which changes the effective electrical resistance of the thin film with respect to an external applied magnetic field. Therefore, the GMR sensor is used to detect the magnetic field perturbation due to the magnetic materials placed in proximity. Since this resistance change is a function of the vertical distance between the magnetic material and the thin-film sensor, this mechanism can be used to detect the vertical distance change of the magnetic material.

Hall Effect sensors are known to one of skill in the art. The Hall Effect sensor utilizes the production of a voltage difference (the Hall voltage) across an electrical conductor, transverse to an electric current in the conductor and a magnetic field perpendicular to the current. Therefore, the Hall Effect sensor is used to detect the magnetic field perturbation due to the magnetic materials placed in proximity. Since this voltage difference change is a function of the vertical distance between the magnetic material and the thin-film sensor, this mechanism can be used to detect the vertical distance change of the magnetic material.

Some magnetic detectors are disclosed in: G. Li et al., "Detection of Single Micron-Sized Magnetic Bead and Magnetic Nanoparticles Using Spin Valve Sensors for Biological Applications," J. Appl. Phys., vol. 93, no. 10, pp. 7557-7559, May 2003; S. Han et al., "A High-Density Magnetoresistive Biosensor Array with Drift-Compensation Mechanism," ISSCC Dig. Tech. Papers, pp. 168-169, February 2007; and Y. Liu et al., "CMOS Mini Nuclear Magnetic Resonance System and its Application for Biomolecular Sensing," ISSCC Dig. Tech. Papers, pp. 140-141, February 2008; P. Besse et al., "Detection of a Single Magnetic Microbead Using a Miniaturized Silicon Hall Sensor," Appl. Phys. Letters, vol 80, no. 22, pp. 4199-4201, June 2002.

Effective inductance-change sensors are described, for example, in co-pending U.S. Patent Application No. 20090267596. Effective inductance-change detectors include, for example, impedance measurement based sensors, transmission line based sensors, and oscillator based sensors, each described in U.S. Patent Application 20090267596. In some embodiments, the sensor is fabricated using CMOS technology, which allows a sensor to be constructed inexpensively.

In one embodiment, the effective inductance-change detector is an oscillator based detector. Resonant structures can be made by combining inductors and capacitors and/or a microwave resonator. Resonant structures include parallel, series, and multi-mode resonators. An oscillator can be based on such resonant structures. An oscillator based on one or more resonators has an oscillation frequency. The oscillation frequency of the oscillator can be measured directly to indicate an inductance(s) (and/or the equivalent inductive part(s)) or change of inductance(s).

One/multiple oscillator(s) can be made based on one/multiple resonator(s) to have one/multiple oscillation frequency/frequencies. The oscillation frequency (frequencies) can also be used to sense both/either the self/mutual inductance(s) (and/or the self/mutual inductive part(s)).

Figure 14:
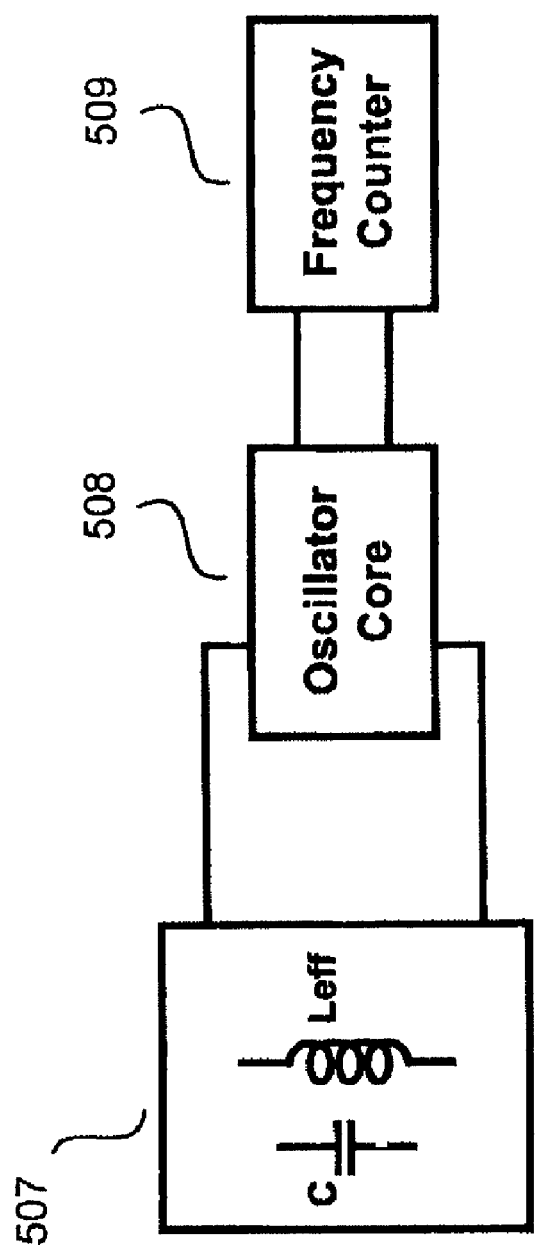
FIG. 14 shows one embodiment of a detection system using an inductance sensor based on an oscillator.

FIG. 14 shows one embodiment of a detector using an inductance sensor based on an oscillator. Block 507 includes the sensing structure whose (self/mutual) inductor (or equivalent self/mutual inductive part) will change its value when magnetic particles are present, and together with capacitors (or equivalent capacitive part), block 507 forms a resonance tank for the oscillator. Block 508, the circuitry for the oscillator core, pumps that power to the lossy tank to maintain a steady oscillation. Block 508 can include cross-coupled transistor pairs, such as have been used in negative-gm oscillator designs, or other suitable feedback structures such as are used in a Colpitts oscillator design. Block 509, a frequency counter, can be an off-the shelf type unit, such as a commercial frequency counter, or can be integrated counter such as an integrated synchronous or asynchronous adder.

Block 508 corresponds to the one or more circuits that can generate an electrical current conducting through the EM structures as well as the one or more circuits to sense the effective inductance and/or a change in effective inductance, while counter block 509 serves as a read-out device.

Figure 15:
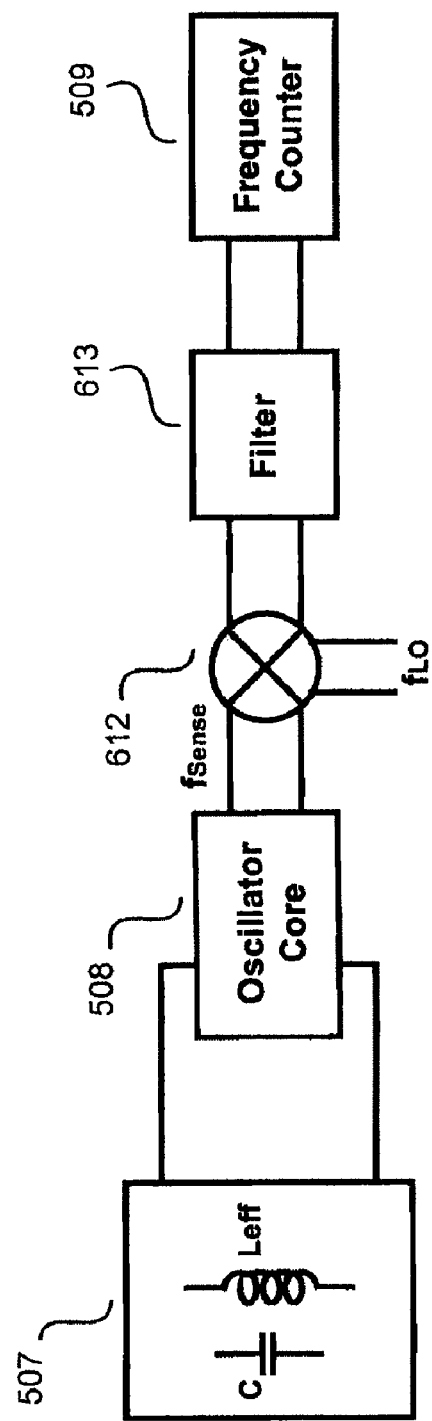
FIG. 15 shows one embodiment of an improved oscillator based sensor.

FIG. 15 shows one embodiment of an oscillator based sensor. Note that blocks 507, 508 and 509 of FIG. 15 are equivalent to the same numbered blocks in FIG. 14. In FIG. 15, an additional mixer 612 mixes $f_{sense}$, the output of oscillator core 508 with a local oscillator frequency, such as an external frequency $f_{LO}$. The oscillation tone $f_{sense}$ is translated by mixing. The mixer 612 output includes the sum and difference frequencies: $f_{sense}+f_{LO}, f_{sense}-f_{LO}$. There are at least two advantages to counting the downconverted tone $f_{sense}-f_{LO}$. First, the sensitivity of the signal frequency sensed by the counter is increased from $\Delta f/f_{sense}$ to $\Delta f/(f_{sense}-f_{LO})$. Second, counting at a lower frequency of $f_{sense}-f_{LO}$, instead of a higher frequency of $f_{sense}$ makes the counter design both more reliable as well as saving electrical power (more energy efficient). Block 613 is used to filter out undesired frequencies, such as the unwanted tone $f_{sense}+f_{LO}$. Thus, it can seen that block 612 and block 613 can be used to reduce the requirements of counter 509 (by lowering the frequency to $f_{sense}-f_{LO}$) as well as to improve the resolution of the frequency read-out. Moreover, although not shown in FIG. 15, multiple mixers and multiple filters can be used for multi-step downconversion.

Using the impedance sensing method described above on a resonator structure, the impedance function linewidth can be fundamentally limited by the quality factor of the EM sensing structure. By contrast, when using an oscillator based measurement as the EM sensing structure, the phase noise linewidth is significantly reduced. Reduction in phase noise linewidth leads to an ultra-high sensor sensitivity which can easily detect a small frequency (inductance) change.

By averaging the measured data, such as the frequency counting results for the oscillator based measurement scheme, the sensor system can achieve an improved noise floor (i.e. improved sensitivity). Also, the sensor can achieve a high sensitivity by use of a low noise oscillator, differential sensing scheme and/or a temperature regulator structures. By choosing an appropriate measurement time T (frequency counting time) for an oscillator-based measurement implementation, a low sensor noise-floor can be achieved.

Figure 16:
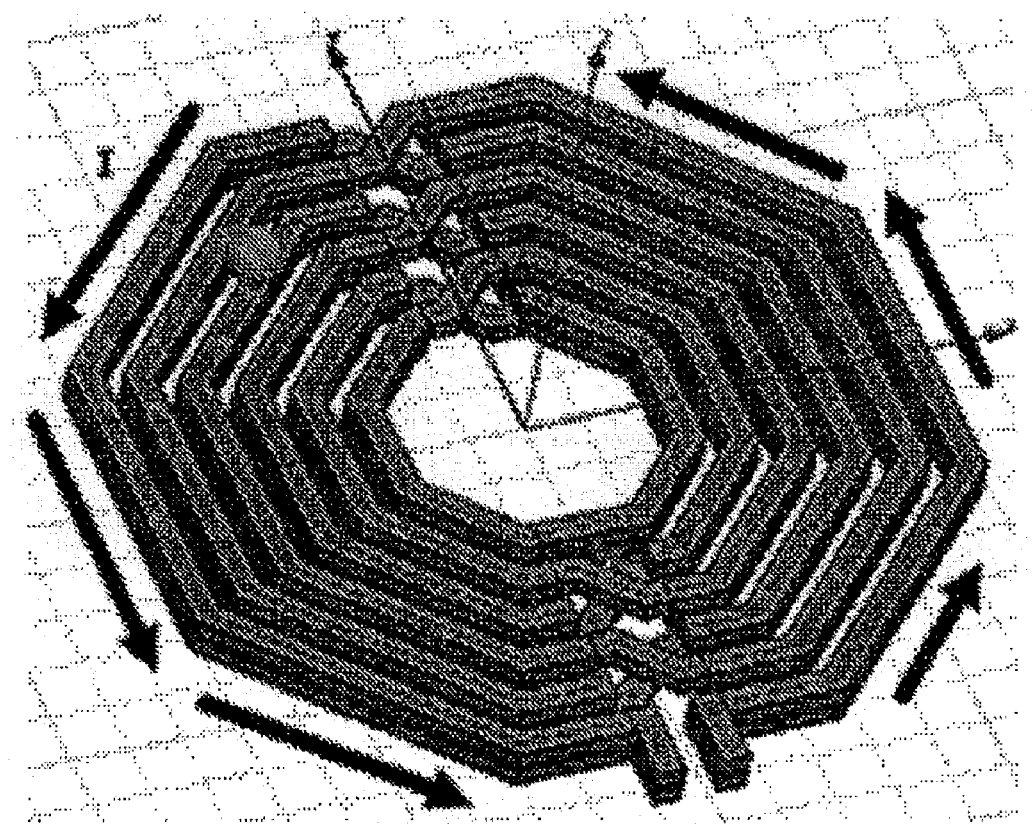
FIG. 16 shows an exemplary inductor structure that can generate a magnetic field to polarize a magnetic particle.

FIG. 16 shows an exemplary structure that generates an induced magnetization M causing a polarization of a magnetic particle. This magnetic field polarizes one or more magnetic particles present in the magnetic field. The exemplary magnetic field generating sensor structure of FIG. 16 uses a spiral 6-turn symmetric inductor. The black arrows show a current I.

In some embodiments, where the detector is a CMOS, multiple sensors can be made on a single chip. Such sensors can be spatially separated to allow detection of multiple analytes or for differential sensing.

Binding Moieties

Binding moieties are chosen based on the analyte being detected. Binding moieties include, for example, proteins, including, for example, antibodies, and nucleic acids. In some embodiments, nucleic acids are used to detect other nucleic acids through hybridization. In some embodiments, nucleic acids are aptamers that can bind a variety of analytes or target molecules.

In some embodiments, a detection device can have two or more binding moieties capable of binding the different regions of the same target molecule. In some embodiments, the binding moieties are each nucleic acid molecules that hybridize to different regions of the same target nucleic acid molecule. The binding moieties can be separated by a linker. In one embodiment, the linker allows binding of the two or more binding moieties to the target molecule simultaneously. In some embodiments, the two or more binding moieties are antibodies linked to a linker.

Figure 8:
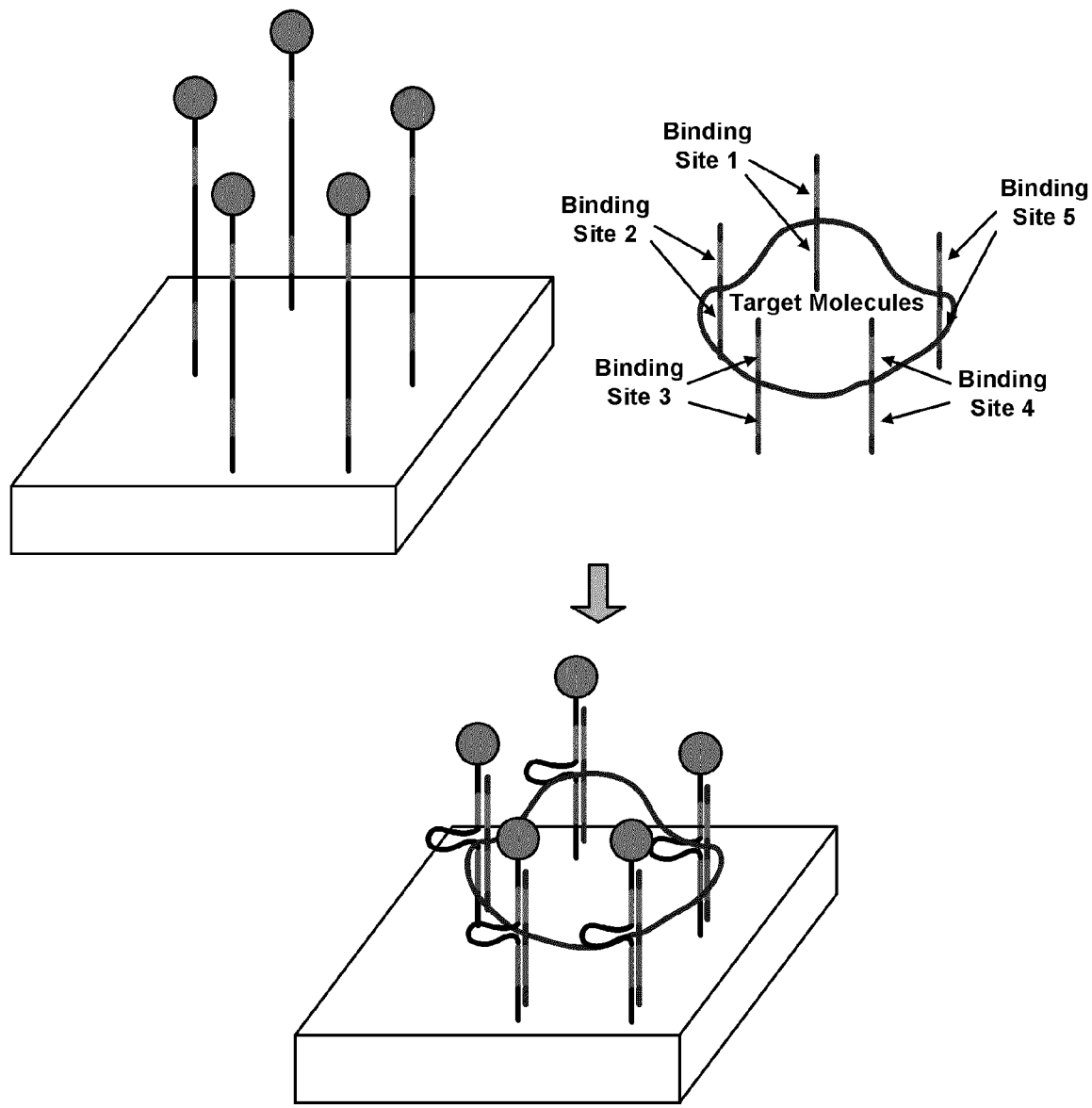
FIG. 8 shows a detection device configured to bind multiple binding sites on the target molecule.
Figure 12:
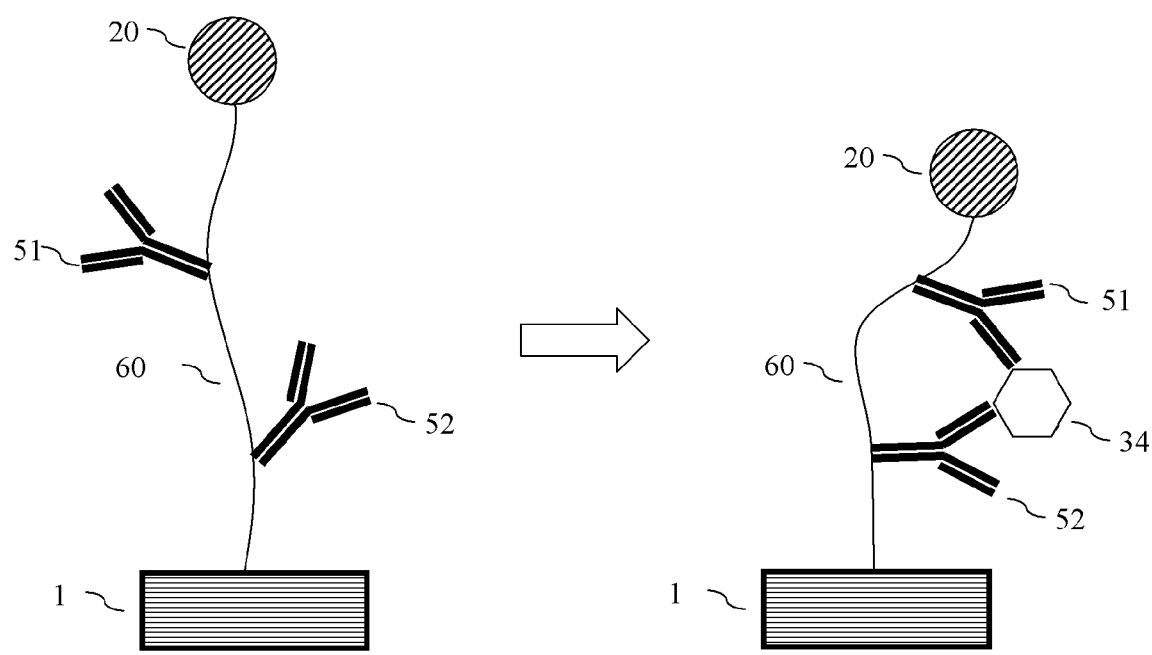
FIG. 12 illustrates a device having two antibody binding moieties linked to an electromagnetic detector, and having an electromagnetic material.

For example, a target molecule with multiple binding sites is demonstrated in FIG. 8, which has 5 binding sites. One binding site is composed of binding moieties 31 and 32 that bind to corresponding regions 36 and 37 on the target molecule. Note that more binding sites can be present by the target molecules. Note that the multiple binding sites on the target molecules can be composed of the same or different types of binding sites. This increase the chance for the target molecules to interact with the probe molecules and also increase the sensor signal strength per target molecule. Another embodiment is shown in FIG. 12, in which a linker with two binding moieties that are antibodies 51 and 52 that are linked to a single linker 60 that connects an electromagnetic detector 1 to electromagnetic material 20. In the embodiment shown in FIG. 8, each antibody 51 and 52 can bind to a single analyte molecule 34, such that binding changes the conformation of linker 60, causing a detectable change in the position of the electromagnetic material.

In some embodiments, a detection device can have can have two or more binding moieties capable of binding to different target molecules or analytes. Such a device can test for the presence of either of two analytes simultaneously.

Nucleic Acid Binding Moieties

Nucleic acid binding moieties can include a variety of backbone modifications, including, for example, peptide nucleic acids (PNAs), phosphotriesters, methylphosphonates. These nucleic acid analogs are known in the art.

In particular, PNAs are discussed in: Nielsen, "DNA analogues with nonphosphodiester backbones," Annu. Rev. Biophys. Biomol. Struct, 1995; 24:167-83; Nielsen et al., "An introduction to peptide nucleic acid," Curr Issues Mol Biol, 1999; 1(1-2):89-104; and Ray et al., "Peptide nucleic acid (PNA): its medical and biotechnical applications and promise for the future," FASEB J., 2000 June; 14(9): 1041-60; all of which are hereby expressly incorporated by reference in their entirety.

Phophotriesters are discussed in: Sung et al., "Synthesis of the human insulin gene. Part II. Further improvements in the modified phosphotriester method and the synthesis of seventeen deoxyribooligonucleotide fragments constituting human insulin chains B and mini-cDNA," Nucleic Acids Res, 1979 Dec. 20; 7(8):2199-212; van Boom et al., "Synthesis of oligonucleotides with sequences identical with or analogous to the 3'-end of 16S ribosomal RNA of *Escherichia coli*: preparation of m-6-2-A-C-C-U-C-C and A-C-C-U-C-m-4-2C via phosphotriester intermediates," Nucleic Acids Res, 1977 March; 4(3):747-59; and Marcus-Sekura et al., "Comparative inhibition of chloramphenicol acetyltransferase gene expression by antisense oligonucleotide analogues having alkyl phosphotriester, methylphosphonate and phosphorothioate linkages," Nucleic Acids Res, 1987 Jul. 24; 15(14):5749-63; all of which are hereby expressly incorporated by reference in their entirety.

Methylphosphonates are discussed in: U.S. Pat. No. 4,469, 863 (Ts'o et al.); Lin et al., "Use of EDTA derivatization to characterize interactions between oligodeoxyribonucleoside methylphosphonates and nucleic acids," Biochemistry, 1989, Feb. 7; 28(3):1054-61; Vyazovkina et al., "Synthesis of specific diastereomers of a DNA methylphosphonate heptamer, d(CpCpApApApCpA), and stability of base pairing with the normal DNA octamer d(TPGPTPTPTPGPGPC)," Nucleic Acids Res, 1994 Jun. 25; 22(12):2404-9; Le Bec et al., "Stereospecific Grignard-Activated Solid Phase Synthesis of DNA Methylphosphonate Dimers," J Org Chem, 1996 Jan. 26; 61(2):510-513; Vyazovkina et al., "Synthesis of specific diastereomers of a DNA methylphosphonate heptamer, d(CpCpApApApCpA), and stability of base pairing with the normal DNA octamer d(TPGPTPTPTPGPGPC)," Nucleic Acids Res, 1994 Jun. 25; 22(12):2404-9; Kibler-Herzog et al., "Duplex stabilities of phosphorothioate, methylphosphonate, and RNA analogs of two DNA 14-mers," Nucleic Acids Res, 1991 Jun. 11; 19(11):2979-86; Disney et al., "Targeting a *Pneumocystis carinii* group I intron with methylphosphonate oligonucleotides: backbone charge is not required for binding or reactivity," Biochemistry, 2000 Jun. 13; 39(23): 6991-7000; Ferguson et al., "Application of free-energy decomposition to determine the relative stability of R and S oligodeoxyribonucleotide methylphosphonates," Antisense Res Dev, 1991 Fall; 1(3):243-54; Thiviyanathan et al., "Structure of hybrid backbone methylphosphonate DNA heteroduplexes: effect of R and S stereochemistry," Biochemistry, 2002 Jan. 22; 41(3):827-38; Reynolds et al., "Synthesis and thermodynamics of oligonucleotides containing chirally pure R(P) methylphosphonate linkages," Nucleic Acids Res, 1996 Nov. 15; 24(22):4584-91; Hardwidge et al., "Charge neutralization and DNA bending by the *Escherichia coli* catabolite activator protein," Nucleic Acids Res, 2002 May 1; 30(9): 1879-85; and Okonogi et al., "Phosphate backbone neutralization increases duplex DNA flexibility: A model for protein binding," PNAS U.S.A., 2002 Apr. 2; 99(7):4156-60; all of which are hereby incorporated by reference.

Hybridizing Nucleic Acids

Nucleic acids can be used as binding moieties that interact with an analyte or target molecule through hybridization. In some embodiments, the binding moieties comprise a nucleotide sequence of about 10 to 50 bases which is able to specifically bind to a given target sequence to form duplexes by complementary hybridization. In an embodiment, the portion of the binding moiety sequences complementary to the target is comprised between about 10 and about 50 bases, preferably between about 15 and about 40 bases and more preferably between about 20 and about 30 bases. This sequence is considered as the specific sequence for the detection.

Figure 9:
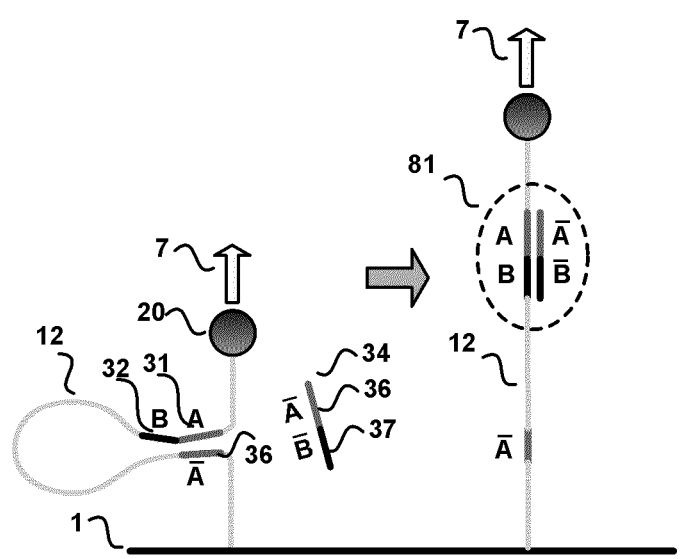
FIG. 9 shows a detection device that implements "negative sensing", where binding of a target molecule to the binding moieties relieves an internal binding between binding moieties on the detector.

In some embodiments, the binding moiety can internally hybridize or can hybridize to another nucleic acid sequence in the detection device (for example, a linker region or another binding moiety). In such embodiments, hybridization of the target molecule will relieve the internal hybridization of the binding moiety. In some embodiments, relief of the internal hybridization will lead to a change in conformation of the detection device. For example, in the embodiment shown in FIG. 9, a nucleic acid immobilized on the surface of detector 1, has two binding moieties 31 and 32. Binding moiety 31 is complementary to a region of the immobilized nucleic acid 36 that also is present on target molecule 34. In the absence of target molecule 34, binding moiety 31 can form a loop region in linker 12. On binding of target molecule 34, binding moieties 31 and 32 bind to regions 36 and 37 of target molecule 34 to form complex 81. On binding, internal hybridization is relieved and the nucleic acid can achieve an extended conformation of linker 12. A force 7 can be applied to particle 20. The change in relative distance of particle 20 from detector 1 can be detected. In such an embodiment, complex 81 is energetically more favorable than the internally hybridized structure. The relative free energies of hybridized nucleic acids can be calculated by one of skill in the art, using for example, the relative nucleotide content of sequences to estimate the free energy of binding. Energies also can be experimentally determined, using for example, helix melting temperatures.

Aptamers

A binding moiety can be an aptamer that binds to a desired analyte or analytes. In some embodiments, the aptamer has an average conformation on binding of the analyte that is different from the conformation in the absence of the analyte.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants (KD) of the aptamer for its ligand as compared to the dissociation constant of the aptamer for other materials in the environment or unrelated molecules in general. A ligand is one which binds to the aptamer with greater affinity than to unrelated material. Typically, the KD for the aptamer with respect to its ligand will be at least about 10-fold less than the KD for the aptamer with unrelated material or accompanying material in the environment. Even more preferably, the KD will be at least about 50-fold less, more preferably at least about 100-fold less, and most preferably at least about 200-fold less. An aptamer will typically be between about 3 and about 300 nucleotides in length. In some embodiments, an aptamer will be between about 5 to 100 nucleotides in length.

Aptamers are known that bind to a variety of molecules. Such aptamers can be used. For example, aptamers are known that bind: isoleucine (Lozupone et al., RNA (2003) Vol. 9, Issue 11, pages 1315-22); Coenzyme A (Saran et al. BMC Evol. Biol. (2003) Vol. 3, Issue 1, pages 26); dopamine (Mannironi et al. Biochemistry (1997) Vol. 36, Issue 32, pages 9726-34); HIV-1 RRE (Boiziau et al. Journal of biological chemistry (1999) Vol. 274, Issue 18, pages 12730-37); ATP (Vaish et al., Biochemistry (2003) Vol. 42, Issue 29, pages 8842-8851); codeine (Win et al., RNA (2006) Vol. 34, Issue 19, pages 5670-82); FAD (Roychowdhury-Saha et al., Biochemistry (2002) Vol. 41, Issue 8, pages 2492-9); Vascular Endothelial Growth Factor (VEGF165) (Ruckman, et al. J. Biol. Chem. (1998) Vol. 273, Issue 32, pages 20556-67); arginine (Tao et al., Biochemistry (1996) Vol. 35, Issue 7, pages 2229-38); S-adenosyle methionine (Burke et al. Nucleic Acids Research (1997) Vol. 25, Issue 10, pages 2020-4); neuroeptide Y (Mendonsa et al., J. Am. Chem. Soc. (2005) Vol. 127, Issue 26, pages 9382-3); human complement C5 (Biesecker et al, Immunopharmacology (1999) Vol. 42, Issue 1-3, pages 219-30); K Ras-Derived Farnesylated Peptide (Gilbert et al. Bioorg. Med. Chem. (1997) Vol. 5, Issue 6, pages 1115-22); *Escherichia coli* rho factor (Schneider et al, FASEB J. (1993) Vol. 7, Issue 1, pages 201-7); Pepocin (Hirao et al., Journal of Biological Chemistry (2000) Vol. 275, Issue 7, pages 4943-8); Ras-binding domain of Raf-1 (Kimotoa et al., FEBS Lett. (1998) Vol. 441, Issue 2, pages 322-6); cellobiose (Yang et al., PNAS (1998) Vol. 95, Issue 10, pages 5462-7); L-arginine (Geiger et al, Nucleic Acids Research (1996) Vol. 24, Issue 6, pages 2755-8); streptavidin (Tahiri-Alaoui et al., Nucleic Acids Res. (2002) Vol. 30, Issue 10, pages e45); cholic acid (Kato et al., Biochim. Biophys. Acta (2000) Vol. 1493, Issue 1-2, pages 12-8); Cyanocobalamin (Lorsch et al., Biochemistry (1994) Vol. 33, Issue 4, pages 973-82); HIV-1 Tar element (Boiziau et al., Antisense Nucleic Acid Drug Dev. (1997) Vol. 7, Issue 4, pages 369-80); Duconge et al., RNA (1999) Vol. 5, Issue 12, pages 1605-14); Tenascin-C (Hicke et al., J. Biol. Chem. (2001) Vol. 276, Issue 52, pages 48644-54); cocaine (Ulrich et al., Proc. Natl. Acad. Sci. USA (1998) Vol. 95, Issue 24, pages 14051-6); S-Adenosylhomocysteine (Gebhardt, Biochemistry (2000) Vol. 39, Issue 24, pages 7255-65); Isoleucine (Legiewicz et al., J. Biol. Chem. (2005)); Sialyl Lewis (Jeong et al., Biochemical and Biophysical Research Communications (2001) Vol. 281, Issue 1, pages 237-43); CD4 (Kraus et al, J. Immunol. (1998) Vol. 160, Issue 11, pages 5209-12); carcinogenic aromatic amines (Brockstedt et al., Biochem. Biophys. Res. Commun. (2004) Vol. 313, Issue 4, pages 1004-8); chitin (Fukusaki et al., Bioorg. Med. Chem. Lett. (2000) Vol. 10, Issue 5, pages 423-5); HCV NS3 protease (Urvil et al., European Journal of Biochemistry (1997) Vol. 248, Issue 1, pages 130-8); streptomycin (Wallace et al., RNA (1998) Vol. 4, Issue 1, pages 112-23); substance P (Eulberg et al., Nucleic Acids Res. (2005) Vol. 33, Issue 4, pages e45); Elongation Factor Tu (Hornung et al., Biochemistry (1998) Vol. 37, Issue, pages 7260-7); camp (Koizumi et al., Biochemistry (2000) Vol. 39, Issue 30, pages 8983-92); Hemagglutinin (Gopinath et al., J Biochem (Tokyo)(2006) Vol. 139, Issue 5, pages 837-46; Misono et al. Anal. Biochem. (2005) Vol. 342, Issue 2, pages 312-7); Raf-1 (Kimoto et al., Eur. J. Biochem. (2002) Vol. 269, Issue 2, pages 697-704); aminoglycoside antibiotics (Wang et al., Biochemistry (1996) Vol. 35, Issue 38, pages 12338-46); Subtilisin (Takeno et al., Journal of Biochemistry (1999) Vol. 125, Issue 6, pages 1115-9); factor VIIa (Thromb. Haemost. (2000) Vol. 84, Issue 5, pages 841-8); thrombin (Liu, et al., Journal of Molecular Recognition (2003) Vol. 16, Issue 1, pages 23-27); 7-methyl-guanosine binding RNA (Haller et al., PNAS (1997) Vol. 94, Issue 16, pages 8521-6); malachite green (Flinders et al., Chembiochem (2004) Vol. 5, Issue 1, pages 62-72); tenascin-C (Daniels, PNAS (2003) Vol. 100, Issue 26, pages 15416-21); Ricin A-chain (Hesselberth et al., Journal of Biological Chemistry (2000) Vol. 275, Issue 7, pages 4937-42).

Aptamers are typically developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

Antibodies

In some embodiments, antibodies are used as binding moieties. Antibodies are known to bind to a wide variety of molecules and can be selected to bind to many desired molecules using techniques known to one of skill in the art.

Although methods of making monoclonal and polyclonal antibodies are well known in the art, preferred methods are briefly described herein. Variations of the following methods will be apparent to one of skill in the art.

For preparation of polyclonal antibodies, the first step is immunization of the host animal with the immunogen or target molecule. To increase the immune response of the host animal, the immunogen may be combined with an adjuvant. Suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include without limitation, rabbits, guinea pigs, other rodents such as mice or rats, sheep, goats, primates and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for a target molecule, is to immunize a suitable host. Suitable hosts include rats, hamsters, mice, monkeys and the like, and are preferably mice. Monoclonal antibodies may be generated using the hybridoma method described by Kohler et al., Nature, 256:495 (1975) or by recombinant DNA methods, such as those described in U.S. Pat. No. 4,816,567.

The immunogen is administered to the host in any convenient manner known in the art. For example, and without limitation, administration may be by subcutaneous injection with adjuvants, nitrocellulose implants comprising the immunogen or intrasplenic injections. Alternatively, lymphocytes may be immunized in vitro. The immunization protocol may be modulated to obtain a desired type of antibody, e.g. IgG or IgM, where such methods are known in the art (Kohler and Milstein, Nature, 256:495 (1975)). Booster immunizations may be made, for example one month after the initial immunization. Animals are bled and analyzed for antibody titer. Boosting may be continued until antibody production plateaus. Following immunization, plasma cells are harvested from the immunized host. Sources of plasma cells include the spleen and lymph nodes, with the spleen being preferred.

The plasma cells are then immortalized by fusion with myeloma cells to produce hybridoma cells. Fusion may be carried out by an electrocell fusion process or by using a suitable fusing agent, such as polyethylene glycol, to form a hybridoma cell (Goding, Monoclonal Antibodies: Principles and Practice, pp. 59-109, Academic Press, 1996). The plasma and myeloma cells are typically fused by combining the cells in a fusion medium usually in a ratio of about 10 plasma cells to 1 myeloma cell, where suitable fusion mediums include a fusion agent, e.g. PEG 1000, and the like. Following fusion, the fused cells will be selected, e.g. by growing on HAT medium.

A variety of myeloma cell lines are available. Preferably, the myeloma cell is HGPRT negative, incapable of producing or secreting its own antibodies, and growth stable. Preferred myeloma cells also fuse efficiently and support stable high-level production of antibody by the selected antibody-producing cells. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol. 133: 3001 (1984); Brodeur et al., Monoclonal Antibody Production Techniques and Applications, pp. 51-63, Marcel Dekker, Inc., New York, [1987]). Specific cell lines of interest include, for example, p3U1, SP 2/0 Ag14, P3.times.63Ag8.653 (Dr. Greenberg, V.A. Hospital).

Representative hybridomas according to the subject invention include those hybridomas that secrete one of the following monoclonal antibodies: MW1, MW2, MW7, MW8 and hMW9. Each of these antibodies is described in detail below.

Following hybridoma cell production, culture supernatant from individual hybridomas is screened for reactivity with the target molecule, using standard techniques. Such screening techniques are well known in the art and include radioimmunoassay (MA), enzyme-linked immunosorent assay (ELISA), dot blot immunoassays, Western blots and the like. The binding affinity of the monoclonal antibody may, for example, be determined by the Scatchard analysis (Munson et al., Anal. Biochem., 107:220 (1980)).

After hybridoma cells secreting antibodies with the desired specificity, affinity and/or activity are selected, the cells may be subcloned by limiting dilution procedures and grown by standard methods (Goding, Monoclonal Antibodies: Principles and Practice, pp. 59-103, Academic Press, 1996). Culture media may be for example DMEM or RPMI-1640 medium. Alternatively, hybridomas may be grown in vitro as ascites tumors in an animal.

The desired antibody may be purified from the supernatants or ascites fluid by conventional techniques, e.g. affinity chromatography using a target molecule bound to an insoluble support, protein A sepharose and the like.

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Mendez et al. (Nature Genetics 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions, and also harbors 800 kb of human .kappa. locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, phage display technology (McCafferty et al., Nature 348, 552-553 [1990]) can be used to produce human antibodies and antibody fragments in vitro, from immunoglobulin variable (V) domain gene repertoires from unimmunized donors.

Binding fragments or binding mimetics of the subject antibodies may also be prepared. These fragments and mimetics preferably share the binding characteristics of the subject antibodies. "Binding characteristics" when used herein include specificity, affinity, avidity, etc. for the a target molecule. In one embodiment antibody fragments, such as Fv and Fab may be prepared by cleavage of the intact protein, e.g. by protease or chemical cleavage. Nucleic acid encoding the antibody fragments or binding mimetics may be identified.

Antibody fragments, such as single chain antibodies or scFvs, may also be produced by recombinant DNA technology where such recombinant antibody fragments retain the binding characteristics of the above antibodies. "Antibody fragments" when used herein refer to a portion of an intact antibody, such as the antigen binding or variable region and may include single-chain antibodies, Fab, Fab', F(ab')$_2$ and Fv fragments, diabodies, linear antibodies, and multispecific antibodies generated from portions of intact antibodies.

Recombinantly produced antibody fragments generally include at least the $V_H$ and $V_L$ domains of the subject antibodies, so as to retain the desired binding characteristics. These recombinantly produced antibody fragments or mimetics may be readily prepared from the antibodies of the present invention using any convenient methodology, such as the methodology disclosed in U.S. Pat. Nos. 5,851,829 and 5,965,371; the disclosures of which are herein incorporated by reference. The antibody fragments or mimetics may also be readily isolated from a human scFvs phage library (Pini et al., Curr. Protein Pept. Sci., 1(2):155-69 (2000)) using a target molecule.

Antibodies can be attached to surfaces, linkers and particles using techniques known to one of skill in the art. For example, antibodies can be linked through sulfhydryl groups on the antibody. In some embodiments, sulfhydryl groups on the antibody are first reacted with crosslinking agents that provide an additional reactive group for attachment to a surface, linker, or particle. Techniques for attachment of antibodies can be found, for example, in: Goding, Monoclonal Antibodies: Principles and Practice, pp. 59-103, Academic Press, (1996); Harlow, E., and Lane, D. (1998) *Antibodies: A Laboratory Manual*. Cold Springs Harbor Laboratory, Cold Springs Harbor, N.Y.; and Hermanson, Greg. Bioconjugate Techniques. Elsevier (2008).

Attachment of Binding Moieties to the Electromagnetic Detector

In some embodiments, the binding moiety is attached to the electromagnetic detector. The attachment can be through a covalent or non-covalent interaction.

Covalent modification of surfaces is known to one of skill in the art. For example, an electromagnetic detector having a gold surface can be modified using sulfur containing binding moiety. In some embodiments, the electromagnetic detector has a silicon nitride, silicon, or glass surface, and the binding moiety is attached through a silane bond. The electromagnetic detector's surface can be modified with silanol compounds to functionalize the surface with reactive groups that are suitable for conjugation to the binding moiety. In some embodiments, the binding moiety will be DNA that has chemical modifications to its 3' and/or 5' end. Such modifications can include thiol groups, amino groups, and others (Iowa DNA Technologies). Binding moieties with chemical modifications can be conjugated to complimentary groups on the surface of the electromagnetic detector. Further, the magnetic probe can be conjugated to the binding moiety via complementary chemical groups as well.

Many strategies for attachment of nucleic acids and proteins to surfaces can be used, including, for example, those disclosed in Hermanson, Greg *Bioconjugate Techniques*, Elsevier (2008).

Figure 13:
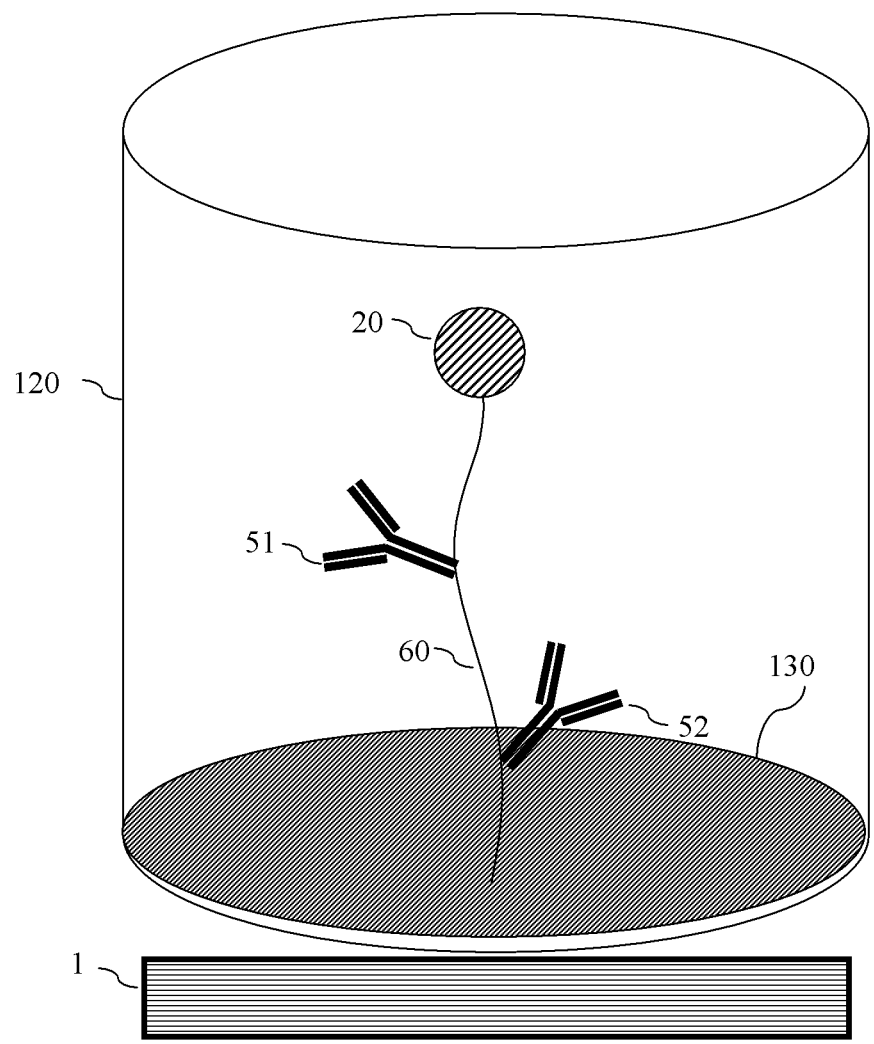
FIG. 13 illustrates a device having a separate electromagnetic detector and vessel containing a binding moiety immobilized to a surface of the vessel and a linked to an electromagnetic material.

In some embodiments, a binding moiety is linked to a surface that is placed adjacent to or near to an electromagnetic detector. In such embodiments, the electromagnetic detector is not in direct contact with the sample containing fluid. The sample containing fluid, with the binding moietie(s) and electromagnetic materials can be included in a separate vessel. In some embodiments, the binding moieties are immobilized on a surface of a dish, plate, slide or other surface, including for example, in 96-well, 356-well, and 1536-well formats. In other embodiments, the binding moieties are immobilized in a microfluidic system. The electromagnetic detectors can be arranged such that the immobilized binding moieties are in physical proximity to the detectors, but not in fluid contact with the detectors. In such an embodiment, the sensors and electronics necessary can be reused, while the sample binding portion disposed of after use. For example, in FIG. 13, vessel 120 having a surface 130 to which linker 60 is attached, is placed on detector 1 which is not in fluid contact with a solution applied to the vessel.

Linkers

In some embodiments, the binding moiety or moities can be attached to the electromagnetic detector (or a surface or substrate that can be placed on or near to the electromagnetic detector) through a linker. Linkers also can be used to attach a binding moiety to an additional binding moiety. Linkers also can be used to link a binding moiety to an electromagnetic material. In some embodiments, a linker is attached to a surface proximal to the electromagnetic detector as well as to an electromagnetic material. In some embodiments, such a linker is attached to one or more binding moieties.

In some embodiments, a linker can be a nucleic acid. In some embodiments, both the binding moieties and the linker are nucleic acids. In such embodiments, the linker generally will not be complementary to a target molecule and does not bind to such target molecule.

Suitable linkers are known to those of skill in the art, and include those from any suitable class of compounds. Polymers or copolymers of organic acids, aldehydes, alcohols, thiols, amines, and the like, are examples of suitable linkers. For example, polymers or copolymers of hydroxy-, amino-, or di-carboxylic acids, such as glycolic acid, lactic acid, sebacic acid, or sarcosine can be used. Alternatively, one can use polymers or copolymers of saturated or unsaturated hydrocarbons such as ethylene glycol, propylene glycol, saccharides, and the like. Linkers also can be nucleic acids. Preferably, the linker should be of an appropriate length that allows an attached binding moiety to interact freely with molecules in a sample solution.

In one embodiment, a linker is attached to the surface of the electromagnetic detector or electromagnetic material by a suitable functional groups on the linker that react with reactive groups already on the solid support. For example, for a solid support that has hydroxyl groups, one can form siloxane bonds by reacting the hydroxyl groups with trichlorosilyl or trisalkoxy groups of a linker. Other suitable linkages, and functional groups that can be reacted to form them, include Schiff base (reaction or amine and aldehyde, with or without subsequent reduction to secondary amine), thioether (reaction of thiol with maleimide or acrylamide), disulfide (activated disulfide with thiol), hydrazone (aldehyde or ketone with hydrazine or hydrazide), semicarbazone (aldehyde or ketone with semicarbazide), oxime (aldehyde or ketone with aminooxyacetyl), thiosemicarbazone (aldehyde or ketone with thiosemicarbazide), and thiazolidine (aldehyde and cystein). The linker can also be attached noncovalently to the solid support. For example, either the support or the linker can be conjugated to a biotin moiety, which will form a strong noncovalent linkage to a conjugation partner that displays avidin. Hydrazine-derivatized linkers are described, for example, in Kirchhoff et al. (2001) J. Combinatorial Chem., 3: 71-77.

It is not intended that the linkers be limited to covalent linkages. Linkers can provide suitable functional groups to form non-covalent, e.g., ionic, interactions between one moiety and another (e.g., a detector or solid support and a binding moiety). For example, a linker bound to a solid support or detector can be biotinylated, while a linker or binding moiety can be coupled with an avidin moiety through a reactive group (or vice-versa).

Linkers can be used in a variety of configurations. For example, a detection device can have a linker separating a binding moiety from the electromagnetic detector. In such an embodiment, the linker is attached to both the electromagnetic detector and the binding moiety. A linker also can be used to separate a plurality of binding moieties. In such an embodiment, the linker can have a linear structure, with multiple binding moieties attached to it, or multiple linkers can be used to separate multiple binding moieties. Linkers also can be used to attach a binding moiety to an electromagnetic material. One of skill in the art will recognize that a detection device can have multiple linkers placed in any of the above configurations.

Electromagnetic Materials

In some embodiments, the detection devices include an electromagnetic material. The material will be selected so that it has electromagnetic properties that can be detected by the electromagnetic detector.

Suitable electromagnetic materials include, for example, magnetic particles, charged particles, particles with a dipole moment, and paramagnetic particles. For example, when the electromagnetic detector is a magnetic detector, the electromagnetic material will generally be a particle that is magnetic. The particle also can have other electromagnetic properties that enable detection by an electromagnetic detector. For example, the elecromagnetic material can have a net charge (either positive or negative) or can have a dipole moment. In such cases, the electromagnetic detector can be used to detect a change of the relative position or orientation of the electromagnetic material relative to the electromagnetic detector. In some embodiments, the electromagnetic material is paramagnetic.

One of skill in the art will recognize that one or more electromagnetic materials can be used. The materials can be used at the terminus of a binding moiety or linker, or can be appended at one or more sites along the length of a binding moiety or linker. For example, where the binding moiety is a nucleic acid, electromagnetic materials can be appended to the backbone of the nucleic acid, at positions selected so as not to interfere with hybridization or other interaction between the nucleic acid and the analyte. Where the binding moiety is a nucleic acid that interacts with an analyte through Watson-Crick base-pairing, electromagnetic materials can be attached, for example, to positions on the backbone or bases that do not significantly perturb the base-pairing interaction.

Suitable magnetic particles include monodisperse superparamagnetic particles disclosed, for example, in U.S. Pat. Nos. 5,512,439 and 4,910,148, as well as SiMAG particles Chemicell GmbH (Berlin, Germany); Iron Oxide Nanocrystals nanoparticles, including those sold by Ocean NanoTech (Springdale, Ark.). Iron particles can be coated with polymer or other coatings, including, for example, polyethylene glycol coatings, or can be functionalized with various reactive groups that enable attachment to a linker or binding moiety.

The particle can be covalently attached to the electromagnetic detector, for example, by attachment to a binding moiety or to a binding moiety that is attached to the electromagnetic detector.

In some embodiments, the electromagnetic material is a chelator. Suitable chelators include metal-binding peptides or proteins. Linkers and binding moieties can be modified to include one or more electromagnetic materials. In one embodiment, a linker or binding moiety has one or more metal-binding peptides, for example, a histidine-rich sequence such as $His_6$. Such a metal-binding peptide can be loaded with metal ions that can be detected by the electromagnetic detector.

In some embodiments, the electromagnetic material is a non-peptide chelator. Any chelator capable of binding a detectable metal ion stably can be used, including, for example, macrocyclic chelators. Macrocyclic chelators include, for example, cyclams, porphyrins, and crown ethers. In some embodiments, the chelator binds a detectable metal ion with an affinity of less than $10^{-4}$ M, less than $10^{-5}$ M, or less than $10^{-6}$ M. Suitable metal ions are magnetic or paramagnetic. In one embodiment, the electromagnetic material is a texaphyrin, including those disclosed in U.S. Pat. Nos. 5,162,509; 5,569,759; 7,449,454; 7,112,671; 6,984,734; 6,638,924; 5,969,111; and 5,837,866.

In some embodiments, the electromagnetic material is a protein that includes one or more metal ions. In one embodiment, the protein is ferritin or a homolog of ferritin.

Analytes

The detection devices can be configured to bind a wide variety of analytes. In some embodiments, the analyte is a: protein, nucleic acid, or small molecule, including, for example, drugs, carbohydrates, lipids, steroids, metabolites, intermediates, cofactors, transition state analogs, ions, metals, nucleic acids, and toxins.

Multiplex Sensing

Detection devices can be configured to bind more than one analyte. In some embodiments, the system includes an array of two or more electromagnetic detectors. Each detector can have one or more binding moieties.

Figure 10:
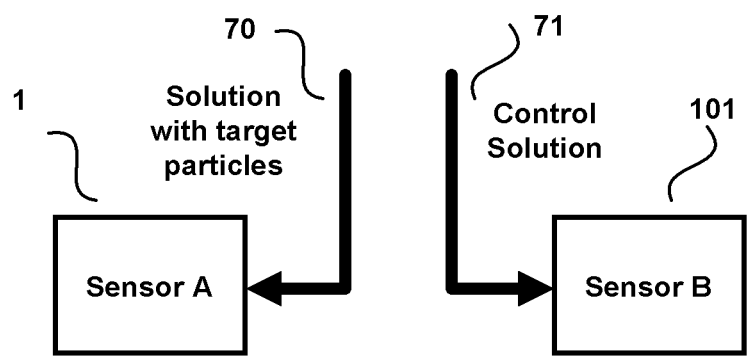
FIG. 10 illustrates a device configured for differential molecular sensing.

In some embodiments, the devices are configured to use differential sensing. In an embodiment shown in FIG. 10, a first sensor 1 is used as the active sensor while a second sensor B 4 is used as a reference. Solution 70 that contains target molecules, is fed into the sensor 1. A control solution 71 is fed into the sensor 101. The control solution can include certain molecules which will interact with the corresponding probes on sensor B, including the target molecule in known amounts. Also the control solutions may only contain buffer solution. Therefore, taking the difference of the two sensors signals provide differential information of the two sensor systems, which suppresses any common-mode response, such as noise or signal-offset presented to both sensors.

In some embodiments, the detection devices are configured in an array having a plurality of electromagnetic detectors, each having one or more binding moieties capable of binding one or more analytes.

Figure 11:
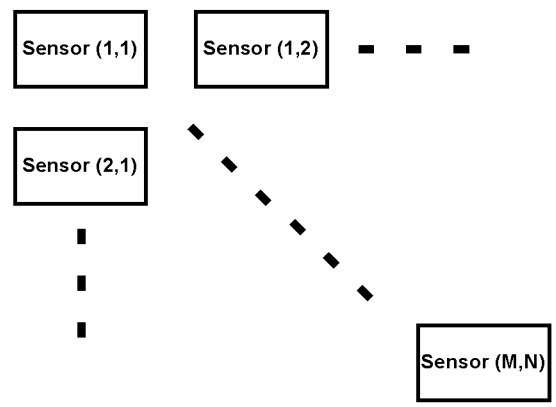
FIG. 11 illustrates an M*N array implementation of the label-free molecular sensors.

In an embodiment shown in FIG. 11, an array of sensors is shown, with each block representing one sensor. Note that any of the sensors in the array can be used as the reference sensors described in the differential sensing. Also, the sensors implemented in the array can essentially have different sensing mechanisms, i.e. different electrical and/or magnetic sensing mechanisms.

An array can be constructed such that a fluid sample applied to the array is in contact with each of the sensors in the array. In another embodiment, each sensor is separated from the other sensors such that a sample applied to one sensor will not interact with another sensor.

EXAMPLES

Example 1

Surface Modification of an Electromagnetic Detector

Prior to surface modification of the electromagnetic detector, the detector will be cleaned by sequential rinses in acetone, ethanol, and distilled water, and finally will be sonicated to remove any debris from its surface. Then, the surface of the electromagnetic detector will be cleaned on a molecular scale by one of two methods: (1) plasma etching with oxygen, set at 3 torr and 100 W for 2.5 minutes, or (2) piranha wash, where the electromagnetic detector is cleansed in a 4:1 mix of sulfuric acid and hydrogen peroxide while heated to 110° C. for 5 minutes.

Following the cleaning, the electromagnetic detector will be functionalized using silane chemistry. The silane is prepared by adding 2% (v/v) triethoxysilyludecanal (TESUD) to a 95%/5% mixture of ethanol and water (Gelest, Inc Product Number SIT1984.0). After the silanol condensation reaction has evolved for 5 minutes, the electromagnetic detector or other substrate is immersed in the solution for 2 hours. The surface is then rinsed repeatedly with ethanol and is baked at 110° C. for 30 minutes. In addition, formation of the silane monolayer can occur through chemical vapor deposition (Hozumi and Shirahata, Surface Science, 2006)

DNA will then be printed directly onto the surface of the electromagnetic detector. The DNA will be chemically modified at both its 3' and 5' ends, making the molecule bifunctional. The 5' end will be functionalized with an amine linker, which can bind covalently to the TESUD-treated surface of the electromagnetic detector through formation of a Schiff base. Subsequent reduction using sodium borohydride stabilizes this bond. The 3' end of the DNA will contain a thiol linker that will be used for covalent attachment to a magnetic particle.

To print the DNA at precise locations on the detector surface, we will use a customized SpotBot3 microarrayer from the Array It Corporation. The customized SpotBot3 includes a vision system that allows the user to teach the robot the locations of specific features of the electromagnetic detector to be printed.

Commercially available functionalized beads will be used for the magnetic particle, such as fluidMAG-amine nanoparticles from Chemicell. These beads will be treated with sulfosuccinimidyl-4-[N-maleimidomethyl]cyclohexane-1-carboxylate (sulfo-SMCC) to change the linker group to a maleimide from an amine. Then, the beads will be attached to the DNA probe strands immobilized on the detector surface through reaction of thiol-labeled DNA with bead-labeled maleimide.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

Incorporation By Reference

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

Equivalents

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A detection device comprising:
   an electromagnetic detector;
   a first binding moiety comprising a first binding site;
   a second binding moiety comprising a second binding site; and an electromagnetic material;

wherein the first binding moiety is attached to the electromagnetic detector prior to binding of an analyte to the first binding moiety, wherein the second binding moiety is attached to the electromagnetic material prior to the binding of the analyte to the second binding moiety, wherein the device is configured such that binding of the analyte to the first binding site and the second binding site changes the relationship between the electromagnetic detector and the electromagnetic material such that the change in the relationship is detected by the electromagnetic detector as a change in electromagnetic field, wherein the analyte is a nucleic acid, and wherein at least one of the first binding moiety and the second moiety is a nucleic acid and internally hybridizes in the absence of the analyte.

2. The device of claim 1, wherein the first binding moiety is covalently linked to the electromagnetic detector.

3. The device of claim 1, wherein the second binding moiety is covalently linked to the electromagnetic material.

4. The device of claim 1, further comprising a magnet, electromagnet, or electrode, wherein the electromagnetic material is situated between the electromagnetic detector and the magnet, electromagnet or electrode.

5. The device of claim 1, wherein the electromagnetic material is buoyant.

6. The device of claim 1, wherein the first binding moiety is covalently linked to the electromagnetic material.

7. The device of claim 1, wherein the electromagnetic material is a charged particle, a magnetic particle, or a particle with a dipole.

8. The device of claim 7, wherein the electromagnetic material is a ferromagnetic bead or a superparamagnetic bead.

9. The device of claim 7, wherein the electromagnetic material is a chelator.

10. The device of claim 7, wherein the electromagnetic material is ferritin.

11. The device of claim 1, wherein the electromagnetic detector produces an electric signal.

12. The device of claim 1, wherein the first binding moiety and the second binding moiety are covalently linked.

13. The device of claim 12, wherein the first binding moiety and the second binding moiety are nucleic acids.

14. The device of claim 1, wherein the electromagnetic detector is a magnetic detector.

15. The device of claim 14, wherein the electromagnetic detector is a GMR, Hall effect, or effective-inductance change magnetic detector.

16. The device of claim 1, wherein at least one of the binding first moiety and the second moiety is an aptamer.

17. The device of claim 1, wherein the first binding moiety and the second binding moiety are the same.

18. The device of claim 1, wherein the first binding moiety and the second binding moiety are different.

19. The device of claim 1, further comprising a linker attached to at least one of the first binding moiety and the second moiety.

* * * * *